US011934583B2

(12) United States Patent
Leaper

(10) Patent No.: US 11,934,583 B2
(45) Date of Patent: Mar. 19, 2024

(54) WEARABLE DATA COMMUNICATION APPARATUS, KITS, METHODS, AND SYSTEMS

(71) Applicant: DATAFEEL INC., Omaha, NE (US)

(72) Inventor: Matthew Robert Leaper, Omaha, NE (US)

(73) Assignee: DATAFEEL INC., Washington, DC (US)

(*) Notice: Subject to any disclaimer, the term of this patent is extended or adjusted under 35 U.S.C. 154(b) by 0 days.

(21) Appl. No.: 18/024,731

(22) PCT Filed: Nov. 2, 2021

(86) PCT No.: PCT/US2021/057634
§ 371 (c)(1),
(2) Date: Mar. 3, 2023

(87) PCT Pub. No.: WO2022/094439
PCT Pub. Date: May 5, 2022

(65) Prior Publication Data
US 2023/0273684 A1  Aug. 31, 2023

Related U.S. Application Data

(60) Provisional application No. 63/107,963, filed on Oct. 30, 2020.

(51) Int. Cl.
G06F 3/041 (2006.01)
G06F 3/01 (2006.01)
(Continued)

(52) U.S. Cl.
CPC .............. *G06F 3/016* (2013.01); *G06F 3/041* (2013.01); *G06F 3/04817* (2013.01); *G06F 3/04883* (2013.01); *G06V 40/13* (2022.01)

(58) Field of Classification Search
CPC ...... G06F 3/016; G06F 3/041; G06F 3/04817; G06F 3/04883; G06F 1/163; G06V 40/13
See application file for complete search history.

(56) References Cited

U.S. PATENT DOCUMENTS 2,088,780 A   8/1937 Follese
2,327,222 A   8/1943 Sell
(Continued)

FOREIGN PATENT DOCUMENTS

AU    2015202395 A1   5/2015
CN    108078548 A     5/2018
(Continued)

OTHER PUBLICATIONS

Ashley Carman, "This ring will vibrate in coordination with your loved one's pulse; They're alive! And not answering your texts!," Circuit Breaker, The Verge, Aug. 10, 2016, https://www.theverge.com/circuitbreaker/2016/8/10/12423956/thetouch-hb-ring-heartrate-pulse.

(Continued)

*Primary Examiner* — Temesghen Ghebretinsae
*Assistant Examiner* — Sosina Abebe

(57) ABSTRACT

A data communication apparatus comprising: a plurality of data communication devices comprising a sensor operable to output contextual data associated with a wearer, a plurality of haptic energy generators operable to output a haptic energy toward skin of the wearer, and a control system operable to maintain a data feedback loop with the wearer by causing the plurality of haptic energy generators to output the haptic energy responsive to one of the contextual data and an external data source in data communication with the control system; an electrical network operable to transmit data and power between the plurality of data communication devices; and a wearable structure comprising a biocompatible material shaped to house the plurality of data commu- (Continued)

nication devices and the electrical network, maintain a plurality of air gaps between the plurality of data communication devices, and define a skin contacting surface that is directly engageable with the skin.

53 Claims, 10 Drawing Sheets

(51) Int. Cl.
*G06F 3/04817* (2022.01)
*G06F 3/04883* (2022.01)
*G06V 40/13* (2022.01)

(56) References Cited

U.S. PATENT DOCUMENTS

| | | |
|---|---|---|
| 3,108,268 A | 10/1963 | Uttal |
| 3,594,787 A | 7/1971 | Ickes |
| 3,848,608 A | 11/1974 | Leonard |
| 4,167,189 A | 9/1979 | Tachi et al. |
| 4,428,368 A | 1/1984 | Torii |
| 4,510,939 A | 4/1985 | Brenman et al. |
| 4,535,784 A | 8/1985 | Rohlicek et al. |
| 4,573,481 A | 3/1986 | Bullara |
| 4,612,934 A | 9/1986 | Borkan |
| 4,628,933 A | 12/1986 | Michelson |
| 4,651,716 A | 3/1987 | Forester et al. |
| 4,676,246 A | 6/1987 | Korenaga |
| 4,837,049 A | 6/1989 | Byers et al. |
| 4,885,565 A | 12/1989 | Embach |
| 4,926,879 A | 5/1990 | Sevrain et al. |
| 4,930,504 A | 6/1990 | Diamantopoulos et al. |
| 5,024,236 A | 6/1991 | Shapiro |
| 5,050,587 A | 9/1991 | Sagara et al. |
| 5,109,844 A | 5/1992 | De Juan et al. |
| 5,150,704 A | 9/1992 | Tatebayashi et al. |
| 5,165,897 A | 11/1992 | Johnson |
| 5,175,459 A | 12/1992 | Danial et al. |
| 5,215,088 A | 6/1993 | Normann et al. |
| 5,259,380 A | 11/1993 | Mendes et al. |
| 5,272,716 A | 12/1993 | Soltz et al. |
| 5,300,097 A | 4/1994 | Lerner et al. |
| 5,304,207 A | 4/1994 | Stromer |
| 5,327,886 A | 7/1994 | Chiu |
| 5,358,503 A | 10/1994 | Bertwell et al. |
| 5,385,503 A | 1/1995 | Stouffer et al. |
| 5,436,622 A | 7/1995 | Gutman et al. |
| 5,449,378 A | 9/1995 | Schouenborg |
| 5,464,436 A | 11/1995 | Smith |
| 5,549,660 A | 8/1996 | Mendes et al. |
| 5,551,949 A | 9/1996 | Kim |
| 5,553,148 A | 9/1996 | Werle |
| 5,569,307 A | 10/1996 | Schulman et al. |
| 5,575,761 A | 11/1996 | Hajianpour |
| 5,578,065 A | 11/1996 | Hattori et al. |
| 5,616,140 A | 4/1997 | Prescott |
| 5,627,548 A | 5/1997 | Woo et al. |
| 5,665,053 A | 9/1997 | Jacobs |
| 5,719,561 A | 2/1998 | Gonzales |
| 5,776,233 A | 7/1998 | Wiedemann et al. |
| 5,779,483 A | 7/1998 | Cho |
| 5,800,479 A | 9/1998 | Thiberg |
| 5,843,074 A | 12/1998 | Cocilovo |
| 5,865,771 A | 2/1999 | Shuto et al. |
| 5,876,427 A | 3/1999 | Chen et al. |
| 5,895,348 A | 4/1999 | Hosaka |
| 5,913,883 A | 6/1999 | Alexander et al. |
| 5,935,155 A | 8/1999 | Humayun et al. |
| 5,944,748 A | 8/1999 | Mager et al. |
| 5,948,006 A | 9/1999 | Mann |
| 5,957,569 A | 9/1999 | Helbig et al. |
| 5,957,960 A | 9/1999 | Chen et al. |
| 6,038,485 A | 3/2000 | Axelgaard |
| 6,045,575 A | 4/2000 | Rosen et al. |
| 6,063,108 A | 5/2000 | Salansky et al. |
| 6,074,411 A | 6/2000 | Lai et al. |
| 6,096,066 A | 8/2000 | Chen et al. |
| 6,099,554 A | 8/2000 | Nordquist et al. |
| 6,104,820 A | 8/2000 | Soza |
| 6,107,466 A | 8/2000 | Hasan et al. |
| 6,156,028 A | 12/2000 | Prescott |
| 6,228,103 B1 | 5/2001 | Grey et al. |
| 6,275,213 B1 | 8/2001 | Tremblay et al. |
| 6,277,085 B1 | 8/2001 | Flynn |
| 6,400,989 B1 | 6/2002 | Eckmiller |
| 6,402,739 B1 | 6/2002 | Neev |
| 6,458,157 B1 | 10/2002 | Suaning |
| 6,547,788 B1 | 4/2003 | Maguire et al. |
| 6,712,613 B2 | 3/2004 | Depta |
| 6,735,480 B2 | 5/2004 | Giuntoli et al. |
| 6,819,312 B2 | 11/2004 | Fish |
| 6,889,090 B2 | 5/2005 | Kreindel |
| 7,013,179 B2 | 3/2006 | Carter et al. |
| 7,077,858 B2 | 7/2006 | Fletcher et al. |
| 7,081,128 B2 | 7/2006 | Hart et al. |
| 7,110,820 B2 | 9/2006 | Tcheng et al. |
| 7,113,177 B2 | 9/2006 | Franzen |
| 7,182,739 B2 | 2/2007 | Kopanic et al. |
| 7,238,162 B2 | 7/2007 | Dehli |
| 7,241,291 B2 | 7/2007 | Kreindel et al. |
| 7,324,094 B2 | 1/2008 | Moilanen et al. |
| 7,336,266 B2 | 2/2008 | Hayward et al. |
| 7,390,157 B2 | 6/2008 | Kramer |
| 7,615,015 B2 | 11/2009 | Glen |
| 7,687,678 B2 | 3/2010 | Jacobs |
| 7,696,860 B2 | 4/2010 | Gilson et al. |
| 7,722,655 B2 | 5/2010 | Lee |
| 7,771,374 B2 | 8/2010 | Slatkine |
| 7,818,061 B1 | 10/2010 | Palmer |
| 7,825,903 B2 | 11/2010 | Anastas et al. |
| 7,988,649 B1 | 8/2011 | Kost |
| 8,013,847 B2 | 9/2011 | Anastas |
| 8,027,491 B2 | 9/2011 | LeDonne |
| 8,139,803 B2 | 3/2012 | Afshar |
| 8,147,533 B2 | 4/2012 | Baxter et al. |
| 8,157,753 B2 | 4/2012 | Nichols |
| 8,170,656 B2 | 5/2012 | Tan et al. |
| 8,175,718 B2 | 5/2012 | Wahlgren et al. |
| 8,203,529 B2 | 6/2012 | Rogowitz et al. |
| 8,308,558 B2 | 11/2012 | Thorner |
| 8,316,166 B2 | 11/2012 | Grant et al. |
| 8,362,882 B2 | 1/2013 | Heubel et al. |
| 8,364,257 B2 | 1/2013 | Eerenbeemd et al. |
| 8,369,944 B2 | 2/2013 | Macho et al. |
| 8,552,847 B1 | 10/2013 | Hill |
| 8,632,576 B2 | 1/2014 | Quisenberry |
| 8,633,907 B2 | 1/2014 | Mahalingam |
| 8,686,951 B2 | 4/2014 | Vartanian et al. |
| 8,696,357 B2 | 4/2014 | AlDossary |
| 8,702,769 B2 | 4/2014 | Eckhouse et al. |
| 8,711,118 B2 | 4/2014 | Short et al. |
| 8,740,960 B2 | 6/2014 | Baxter et al. |
| 8,766,786 B2 | 7/2014 | Radivojevic |
| 8,767,996 B1 | 7/2014 | Lin et al. |
| 8,917,167 B1 | 12/2014 | Selker |
| 8,922,503 B2 | 12/2014 | Ciesla et al. |
| 8,965,500 B2 | 2/2015 | Macho et al. |
| 9,008,794 B2 | 4/2015 | Alexandre |
| 9,024,874 B2 | 5/2015 | Stetten et al. |
| 9,042,971 B2 | 5/2015 | Brumback et al. |
| 9,046,919 B2 | 6/2015 | Niknejad |
| 9,053,617 B2 | 6/2015 | Ramstein et al. |
| 9,064,387 B2 | 6/2015 | Bhatia et al. |
| 9,078,065 B2 | 7/2015 | Karam et al. |
| 9,083,821 B2 | 7/2015 | Hughes |
| 9,092,953 B1 | 7/2015 | Mortimer et al. |
| 9,092,954 B2 | 7/2015 | Visitacion et al. |
| 9,095,359 B2 | 8/2015 | Behnke et al. |
| 9,170,650 B2 | 10/2015 | Ramstein et al. |
| 9,195,350 B2 | 11/2015 | Radivojevic et al. |
| 9,198,792 B2 | 12/2015 | Skahan et al. |
| 9,213,408 B2 | 12/2015 | Gandhi et al. |
| 9,254,382 B2 | 2/2016 | Ahmad et al. |

(56) References Cited

U.S. PATENT DOCUMENTS

| | | |
|---|---|---|
| 9,274,603 B2 | 3/2016 | Modarres et al. |
| 9,282,893 B2 | 3/2016 | Longinotti-Buitoni et al. |
| 9,295,607 B2 | 3/2016 | Rosenberg |
| 9,308,363 B2 | 4/2016 | Goroszeniuk et al. |
| 9,311,792 B2 | 4/2016 | Kosonen et al. |
| 9,314,650 B2 | 4/2016 | Rosenberg et al. |
| 9,333,144 B2 | 5/2016 | Baxter et al. |
| 9,333,377 B2 | 5/2016 | Rosenberg |
| 9,364,667 B1 | 6/2016 | Dinsmoor et al. |
| 9,375,345 B2 | 6/2016 | Levinson et al. |
| 9,407,130 B2 | 8/2016 | Garcia et al. |
| 9,408,316 B2 | 8/2016 | Bailey et al. |
| 9,417,694 B2 | 8/2016 | Birnbaum et al. |
| 9,454,915 B2 | 9/2016 | Aldossary et al. |
| 9,466,187 B2 | 10/2016 | Grant et al. |
| 9,468,847 B2 | 10/2016 | Bekri |
| 9,504,826 B2 | 11/2016 | Flyash et al. |
| 9,553,625 B2 | 1/2017 | Hatanaka et al. |
| 9,561,357 B2 | 2/2017 | Hall et al. |
| 9,582,034 B2 | 2/2017 | Badinski et al. |
| 9,582,035 B2 | 2/2017 | Connor |
| 9,582,072 B2 | 2/2017 | Connor |
| 9,585,687 B2 | 3/2017 | Tenenbaum et al. |
| 9,607,492 B2 | 3/2017 | Churovich |
| 9,619,034 B2 | 4/2017 | Birnbaum et al. |
| 9,623,907 B2 | 4/2017 | Marti et al. |
| 9,626,845 B2 | 4/2017 | Eagleman et al. |
| 9,652,946 B2 | 5/2017 | Ramstein et al. |
| 9,669,233 B2 | 6/2017 | Quisenberry et al. |
| 9,672,701 B2 | 6/2017 | Evreinov et al. |
| 9,672,791 B2 | 6/2017 | Kapinos et al. |
| 9,754,078 B2 | 9/2017 | Ramsay et al. |
| 9,754,464 B1 | 9/2017 | Sinkov |
| 9,829,977 B2 | 11/2017 | Heubel et al. |
| 9,884,179 B2 | 2/2018 | Bouton et al. |
| 9,898,085 B2 | 2/2018 | Saboune et al. |
| 9,936,900 B2 | 4/2018 | Chang et al. |
| 9,940,811 B2 | 4/2018 | Chang et al. |
| 9,943,698 B2 | 4/2018 | Chase et al. |
| 9,950,147 B2 | 4/2018 | Mehta |
| 9,961,435 B1 | 5/2018 | Goyal et al. |
| 10,019,912 B2 | 7/2018 | Eagleman et al. |
| 10,039,928 B2 | 8/2018 | Hyde et al. |
| 10,058,476 B2 | 8/2018 | Baxter et al. |
| 10,070,799 B2 | 9/2018 | Ang et al. |
| 10,080,906 B2 | 9/2018 | Schwarz et al. |
| 10,111,010 B2 | 10/2018 | Alexiou et al. |
| 10,123,937 B2 | 11/2018 | Pisharodi et al. |
| 10,181,331 B2 | 1/2019 | Eagleman et al. |
| 10,198,076 B2 | 2/2019 | Eagleman et al. |
| 10,200,332 B2 | 2/2019 | Wu et al. |
| 10,216,278 B2 | 2/2019 | Nakamura et al. |
| 10,234,934 B2 | 3/2019 | Connor |
| 10,255,771 B2 | 4/2019 | Baron et al. |
| 10,275,029 B2 | 4/2019 | Jones et al. |
| 10,285,902 B2 | 5/2019 | Pamplin et al. |
| 10,321,873 B2 | 6/2019 | Connor |
| 10,371,544 B2 | 8/2019 | Yoo et al. |
| 10,384,076 B2 | 8/2019 | Wagenaar et al. |
| 10,456,604 B2 | 10/2019 | Cheatham, III et al. |
| 10,524,978 B2 | 1/2020 | Marton et al. |
| 10,589,087 B2 | 3/2020 | Tyler et al. |
| 10,625,074 B2 | 4/2020 | Rosenbluth et al. |
| 10,699,538 B2 | 6/2020 | Novich et al. |
| 10,748,448 B2 | 8/2020 | Knott et al. |
| 10,828,504 B2 | 11/2020 | Blendermann |
| 10,888,708 B2 | 1/2021 | Stephens et al. |
| 10,945,878 B2 | 3/2021 | Deng et al. |
| 11,247,039 B2 | 2/2022 | Prouza et al. |
| 11,253,717 B2 | 2/2022 | Schwarz et al. |
| 11,439,841 B2 | 9/2022 | Zimmerman |
| 11,464,993 B2 | 10/2022 | Schwarz et al. |
| 11,701,253 B2 | 7/2023 | Black et al. |
| 11,712,367 B2 | 8/2023 | Simons et al. |
| 2001/0043847 A1 | 11/2001 | Kramer |
| 2002/0143373 A1 | 10/2002 | Courtnage et al. |
| 2003/0023297 A1 | 1/2003 | Byers et al. |
| 2003/0032900 A1 | 2/2003 | Ella |
| 2003/0083599 A1 | 5/2003 | Kitov |
| 2003/0181116 A1 | 9/2003 | Heerden et al. |
| 2003/0212350 A1 | 11/2003 | Tadlock |
| 2003/0187488 A1 | 12/2003 | Kreindel et al. |
| 2004/0039254 A1* | 2/2004 | Stivoric ................. A61B 5/389 600/300 |
| 2004/0040800 A1 | 3/2004 | Anastas et al. |
| 2004/0082886 A1 | 4/2004 | Timpson |
| 2004/0210122 A1 | 10/2004 | Sieburg |
| 2004/0241623 A1 | 12/2004 | Lenay et al. |
| 2004/0260211 A1 | 12/2004 | Maalouf |
| 2005/0078846 A1 | 4/2005 | Single |
| 2005/0177093 A1 | 8/2005 | Barry et al. |
| 2006/0036201 A1 | 2/2006 | Cohen |
| 2006/0041207 A1 | 2/2006 | Gross |
| 2006/0052695 A1 | 3/2006 | Adam |
| 2006/0116611 A1 | 6/2006 | Richter |
| 2006/0135890 A1 | 6/2006 | Tsai |
| 2006/0247754 A1 | 11/2006 | Greenberg et al. |
| 2006/0264926 A1 | 11/2006 | Kochamba |
| 2007/0010810 A1 | 1/2007 | Kochamba |
| 2007/0016425 A1 | 1/2007 | Ward |
| 2007/0027411 A1 | 2/2007 | Ella et al. |
| 2007/0063849 A1 | 3/2007 | Rosella et al. |
| 2007/0255187 A1 | 11/2007 | Branch |
| 2007/0255355 A1 | 11/2007 | Altshuler et al. |
| 2008/0014011 A1 | 1/2008 | Rossen |
| 2008/0023597 A1 | 1/2008 | Wyner et al. |
| 2008/0188911 A1 | 8/2008 | Chao |
| 2008/0195000 A1 | 8/2008 | Spooner et al. |
| 2008/0215039 A1 | 9/2008 | Slatkine et al. |
| 2009/0048547 A1 | 2/2009 | Chen |
| 2009/0076421 A1 | 3/2009 | Grant, Jr. |
| 2009/0098519 A1 | 4/2009 | Byerly |
| 2009/0112134 A1 | 4/2009 | Avni |
| 2009/0120105 A1 | 5/2009 | Ramsay et al. |
| 2009/0131840 A1 | 5/2009 | Lee |
| 2009/0143706 A1 | 6/2009 | Acosta |
| 2009/0171251 A1 | 7/2009 | Rybyanets et al. |
| 2009/0180646 A1 | 7/2009 | Vulfson et al. |
| 2009/0221938 A1 | 9/2009 | Rosenberg et al. |
| 2010/0004536 A1 | 1/2010 | Rosenberg |
| 2010/0016761 A1 | 1/2010 | Rosenberg |
| 2010/0042020 A1 | 2/2010 | Ben-Ezra |
| 2010/0069800 A1 | 3/2010 | Hsu |
| 2010/0073150 A1 | 3/2010 | Olson et al. |
| 2010/0134327 A1 | 6/2010 | Dinh et al. |
| 2010/0141407 A1 | 6/2010 | Heubel et al. |
| 2010/0145242 A1 | 6/2010 | Tsai |
| 2010/0145425 A1 | 6/2010 | Jung et al. |
| 2010/0162109 A1 | 6/2010 | Chatterjee et al. |
| 2010/0204619 A1 | 8/2010 | Rosenberg |
| 2010/0259472 A1 | 10/2010 | Radivojevic et al. |
| 2010/0292746 A1 | 11/2010 | Gorham |
| 2010/0298745 A1 | 11/2010 | Liu et al. |
| 2010/0304864 A1 | 12/2010 | Johnson et al. |
| 2010/0305495 A1 | 12/2010 | Anderson et al. |
| 2011/0004261 A1 | 1/2011 | Sham et al. |
| 2011/0046523 A1 | 2/2011 | Altshuler et al. |
| 2011/0148607 A1 | 6/2011 | Zeleny |
| 2011/0166559 A1 | 7/2011 | Eckhouse et al. |
| 2011/0270140 A1 | 11/2011 | Israeli |
| 2012/0010603 A1 | 1/2012 | Milner et al. |
| 2012/0023785 A1 | 2/2012 | Barnes et al. |
| 2012/0035513 A1 | 2/2012 | Afshar |
| 2012/0070805 A1 | 3/2012 | Wong et al. |
| 2012/0123304 A1 | 5/2012 | Rybyanets |
| 2012/0232780 A1 | 9/2012 | Delson et al. |
| 2012/0253236 A1 | 10/2012 | Snow et al. |
| 2012/0253416 A1 | 10/2012 | Erez et al. |
| 2012/0277587 A1 | 11/2012 | Adanny et al. |
| 2013/0131559 A1 | 5/2013 | Vandenbelt et al. |
| 2013/0178764 A1 | 7/2013 | Eckhouse et al. |
| 2013/0202674 A1 | 8/2013 | Ericson |
| 2013/0204169 A1 | 8/2013 | Poepperling et al. |
| 2013/0218456 A1 | 8/2013 | Zelek et al. |

(56) References Cited

U.S. PATENT DOCUMENTS

| | | |
|---|---|---|
| 2013/0331913 A1 | 12/2013 | Levi et al. |
| 2014/0007957 A1 | 1/2014 | Vendramini |
| 2014/0036053 A1 | 2/2014 | Clingman et al. |
| 2014/0070957 A1 | 3/2014 | Longinotti-Buitoni et al. |
| 2014/0085077 A1 | 3/2014 | Luna et al. |
| 2014/0143737 A1 | 5/2014 | Mistry et al. |
| 2014/0163439 A1 | 6/2014 | Uryash et al. |
| 2014/0172062 A1 | 6/2014 | Yoon |
| 2014/0180181 A1 | 6/2014 | Oepen et al. |
| 2014/0184384 A1 | 7/2014 | Zhu et al. |
| 2014/0198034 A1 | 7/2014 | Bailey et al. |
| 2014/0198035 A1 | 7/2014 | Bailey et al. |
| 2014/0206947 A1 | 7/2014 | Isserow et al. |
| 2014/0206976 A1 | 7/2014 | Thompson et al. |
| 2014/0214206 A1 | 7/2014 | Steinberg et al. |
| 2014/0221879 A1 | 8/2014 | Chu |
| 2014/0266570 A1 | 9/2014 | Sharma et al. |
| 2014/0266571 A1 | 9/2014 | Sharma et al. |
| 2014/0276271 A1 | 9/2014 | Stryker et al. |
| 2014/0326241 A1 | 11/2014 | Martin et al. |
| 2015/0038886 A1 | 2/2015 | Snow |
| 2015/0045702 A1 | 2/2015 | Lin |
| 2015/0105129 A1 | 4/2015 | Chapman |
| 2015/0201181 A1 | 7/2015 | Moore et al. |
| 2015/0235529 A1 | 8/2015 | Deschamps |
| 2015/0257970 A1 | 9/2015 | Mücke et al. |
| 2015/0265214 A1* | 9/2015 | De Kok ............... A61B 5/6843 29/846 |
| 2015/0283022 A1 | 10/2015 | Lee et al. |
| 2015/0283026 A1 | 10/2015 | Rosenberg |
| 2015/0290454 A1 | 10/2015 | Tyler et al. |
| 2015/0306373 A1* | 10/2015 | Bouton ................ G06F 3/015 607/148 |
| 2015/0321000 A1 | 11/2015 | Rosenbluth et al. |
| 2015/0335288 A1 | 11/2015 | Toth et al. |
| 2015/0339899 A1 | 11/2015 | Ozaki et al. |
| 2015/0351690 A1 | 12/2015 | Toth et al. |
| 2015/0364018 A1 | 12/2015 | Mirov et al. |
| 2015/0366504 A1 | 12/2015 | Connor |
| 2016/0012688 A1 | 1/2016 | Eagleman et al. |
| 2016/0012689 A1 | 1/2016 | Evreinov et al. |
| 2016/0018920 A1 | 1/2016 | Deokar et al. |
| 2016/0095789 A1 | 4/2016 | Baxter et al. |
| 2016/0101010 A1 | 4/2016 | Hsu |
| 2016/0129248 A1 | 5/2016 | Creasey et al. |
| 2016/0136040 A1 | 5/2016 | Li |
| 2016/0138144 A1 | 5/2016 | Olsérius et al. |
| 2016/0165965 A1 | 6/2016 | Ellis et al. |
| 2016/0187977 A1 | 6/2016 | Cruz-Hernandez et al. |
| 2016/0195928 A1* | 7/2016 | Wagner ................ G06F 1/163 345/156 |
| 2016/0235980 A1 | 8/2016 | Berman et al. |
| 2016/0235983 A1 | 8/2016 | Berman et al. |
| 2016/0246378 A1 | 8/2016 | Sampanes et al. |
| 2016/0255733 A1* | 9/2016 | Jung ................. G04G 21/04 361/759 |
| 2016/0267344 A1 | 9/2016 | Yamamoto |
| 2016/0302721 A1 | 10/2016 | Wiedenhoefer et al. |
| 2016/0338644 A1 | 11/2016 | Connor |
| 2016/0346153 A1 | 12/2016 | Hodges et al. |
| 2016/0349790 A1 | 12/2016 | Connor |
| 2016/0360974 A1 | 12/2016 | Lange |
| 2017/0004685 A1 | 1/2017 | Karsten |
| 2017/0011602 A1 | 1/2017 | Brav et al. |
| 2017/0043150 A1 | 2/2017 | Kim |
| 2017/0080255 A1 | 3/2017 | Law et al. |
| 2017/0095692 A1 | 4/2017 | Chang et al. |
| 2017/0095693 A1 | 4/2017 | Chang et al. |
| 2017/0098350 A1 | 4/2017 | Ebeling et al. |
| 2017/0156662 A1 | 6/2017 | Goodall et al. |
| 2017/0188894 A1 | 7/2017 | Chang et al. |
| 2017/0221323 A1 | 8/2017 | Nakamura et al. |
| 2017/0249810 A1 | 8/2017 | Zerick et al. |
| 2017/0273601 A1 | 9/2017 | Wang et al. |
| 2017/0304646 A1 | 10/2017 | Pryor et al. |
| 2018/0015299 A1 | 1/2018 | Kawa |
| 2018/0021579 A1 | 1/2018 | Kahana et al. |
| 2018/0081439 A1 | 3/2018 | Daniels |
| 2018/0207056 A1 | 7/2018 | Howard et al. |
| 2018/0243161 A1 | 8/2018 | Lenke |
| 2018/0296166 A1 | 10/2018 | LeBoeuf et al. |
| 2018/0303702 A1 | 10/2018 | Novich et al. |
| 2018/0307314 A1 | 10/2018 | Connor |
| 2019/0064924 A1 | 2/2019 | Nocon |
| 2019/0076643 A1 | 3/2019 | Siegle et al. |
| 2019/0105101 A1 | 4/2019 | Narisawa |
| 2019/0125262 A1 | 5/2019 | Markel |
| 2019/0151604 A1 | 5/2019 | Harper et al. |
| 2019/0183388 A1 | 6/2019 | Cohen et al. |
| 2019/0188976 A1* | 6/2019 | Aleksov ................ G06F 3/01 |
| 2019/0343205 A1 | 11/2019 | Clausen |
| 2019/0350752 A1 | 11/2019 | Aguiar et al. |
| 2020/0121550 A1 | 4/2020 | Elliot |
| 2020/0163572 A1 | 5/2020 | Mann |
| 2020/0174583 A1* | 6/2020 | Wang ................ G06F 3/011 |
| 2020/0186104 A1 | 6/2020 | Honda et al. |
| 2020/0245931 A1 | 8/2020 | Chmelik |
| 2020/0246520 A1 | 8/2020 | Chang |
| 2020/0253485 A1* | 8/2020 | Kang ................ A61B 5/021 |
| 2022/0347010 A1 | 11/2022 | Kerth et al. |
| 2023/0118736 A1 | 4/2023 | Yildirim et al. |
| 2023/0185376 A1* | 6/2023 | Sembaluk ............ A61M 21/00 345/156 |

FOREIGN PATENT DOCUMENTS

| | | |
|---|---|---|
| EP | 0556999 A1 | 8/1993 |
| EP | 2450075 A1 | 5/2012 |
| EP | 2203797 B1 | 7/2014 |
| EP | 2506773 B1 | 8/2018 |
| EP | 3003473 B1 | 8/2018 |
| EP | 2790088 B1 | 5/2019 |
| JP | 4143114 B2 | 6/2008 |
| JP | 6178566 B2 | 8/2017 |
| JP | 6652164 B2 | 2/2020 |
| JP | 2022050711 A | 2/2023 |
| KR | 101064115 B1 | 9/2011 |
| KR | 101315403 B1 | 10/2013 |
| KR | 101319429 B1 | 10/2013 |
| WO | 0240095 A1 | 5/2002 |
| WO | 2013118122 A1 | 8/2013 |
| WO | 2014117125 A1 | 7/2014 |
| WO | 2015083183 A1 | 6/2015 |
| WO | 2017158583 A1 | 9/2017 |
| WO | 2017173436 A1 | 10/2017 |
| WO | 2018013835 A1 | 1/2018 |
| WO | 2018048907 A1 | 3/2018 |
| WO | 2019083863 A1 | 5/2019 |

OTHER PUBLICATIONS

David Eagleman, "Can we create new senses for humans?," Transcript of TED Talk, available at: https://www.ted.com/talks/david_eagleman_can_we_create_new_senses_for_humans/transcript?language=en (last accessed May 17, 2022).

Iwamoto et al., "Non-contact Method for Producing Tactile Sensation Using Airborne Ultrasound", Eurohaptics 2008, LNCS 5024, pp. 504-513, http://www.researchgate.net/publication/221011909_Non-contact_Method_for_Producing_Tactile_Sensation_Using_Airborne_Ultrasound.

Maereg et al., "Wearable Vibrotactile Haptic Device for Stiffness Discrimination during Virtual Interactions," Journal of Frontiers in Robotics and AI, vol. 4, 2017, https://www.frontiersin.org/article/10.3389/frobt.2017.00042.

Novich et al., "Using space and time to encode vibrotactile information: toward an estimate of the skin's achievable throughput," Experimental Brain Research. 233, p. 2777-2788(2015). available at: Http://link.springer.com/article/10.1007/s00221-015-4346-1.

Seneviratne et al., "A Survey of Wearable Devices and Challenges," Article, IEEE Communications Surveys & tutorials, Jul. 2017, (52 pages), (99)1-1, available at: http://www.researchgate.net/publications/318717275_A_Survey_of_Wearable_Devices_and_Challenges.

(56) References Cited

OTHER PUBLICATIONS

Shull et al., "Haptic wearables as sensory replacement, sensory augmentation andtrainer—a review," Journal of NeuroEngineering and Rehabilitation, vol. 12, Article #59, 2015, https://doi.org/10.1186/s12984-015-0055-z.
International Search Report and Written Opinion for Patent Application No. PCT/US21/57634 dated Mar. 4, 2022 (10 pages).

* cited by examiner

WEARABLE DATA COMMUNICATION APPARATUS, KITS, METHODS, AND SYSTEMS

TECHNICAL FIELD

Aspects of the present disclosure generally relate to communication devices, methods, and systems. Particular aspects relate to wearable data communication apparatus, kits, methods, and systems operable to maintain one or more data feedback loops.

BACKGROUND

Human performance advantages may be obtained with wearable technologies. Most wearable technologies are screen dependent, making them sources of distraction that can prevent a user from effectively utilizing their eyes to safely navigate their environment. Single and multi-energy haptic technologies have been developed to facilitate non-visual communications with a user when positioned on or adjacent their skin. Aspects described herein may be utilized to better position these technologies on the skin and further optimize their communicative abilities with the user.

SUMMARY

Numerous aspects are described in this disclosure. One aspect is a data communication apparatus. The apparatus may be wearable on or adjacent skin of a wearer. For example, the apparatus may comprise: a plurality of data communication devices comprising a sensor operable to output contextual data associated with the wearer, a plurality of haptic energy generators operable to output a haptic energy toward the skin of the wearer, and a control system operable to maintain a data feedback loop (or "haptic loop") with the wearer by causing the plurality of haptic energy generators to output the haptic energy responsive to one of the contextual data and an external data source in data communication with the control system; an electrical network operable to transmit data and power between the plurality of data communication devices; and a wearable structure comprising a biocompatible material shaped to house the plurality of data communication devices and the electrical network, maintain a plurality of air gaps between the plurality of data communication devices, and define a skin contacting surface that is directly engageable with the skin.

The sensor may comprise a plurality of sensors operable to output the contextual data. Each device of the plurality of data communication devices may comprise: one sensor of the plurality of sensors; and one generator of the plurality of haptic generators. The sensor comprises a physiological sensor operable to output a physiological portion of the contextual data. The physiological sensor may be oriented toward the skin of the wearer. A portion of the physiological sensor may be located on or adjacent the skin.

The physiological sensor may be operable to detect one or more of a blood pressure, a body temperature, a heart rate, a perspiration rate, and a toxicity level of the wearer.

The sensor may comprise an environmental sensor operable to output additional contextual data associated with the wearer or their environment. The environmental sensor may be operable to detect a chemical, electrical, or physical measure of the wearer or their environment. The environmental sensor may be oriented away from the skin of the wearer. The environmental sensor may comprise one or more of an optical sensor, a photo-sensing transistor, and a camera. The plurality of data communication devices may comprise a touchscreen and the environmental sensor may be embedded within an electronic visual display of the touchscreen. The environmental sensor may comprise one or both of a geolocating technology and a motion sensing technology.

The plurality of haptic energy generators comprise a single energy haptic communication technology or a multi-energy haptic communication technology. The plurality of haptic energy generators comprise electromagnetic components operable to output the haptic energy. The control system may comprise a controller of one of the data communication devices. Each data communication device may comprise a controller and the control system may comprise one or more of the controllers of the data communication devices. Each data communication device may comprise a controller, the controllers of the data communication device may be located at different locations and in data communication with one another via the electrical network, and the control system may comprise a distributed computing system with individual processing resources comprising the controllers of the data communication devices. The individual processing elements of the distributed computing system may comprise the external data source.

The plurality of data communication devices may be removably housed in the wearable structure. The wearable structure may define a plurality of bays and the plurality of data communication devices may be removably housed in the plurality of bays to facilitate repairing and upgrading the apparatus. Each device of the plurality of data communication devices may comprise a conductor that electrically engages the electrical network when that device is housed in one bay of the plurality of bays. The conductors of the plurality of data communication devices may be interchangeably engageable with the electric network when housed in any of the plurality of bays. The electrical network may comprise a plurality of conductive materials spanning between the plurality of communication devices. The plurality of conductive materials may comprise metallic wires or electrically conductive filaments. The electrical network may comprise graphene. The electrical network may be 3D printed from the graphene.

The biocompatible material may comprise a silicone. The biocompatible structure may define a plurality of nodes and a plurality of cords shaped to house the plurality of data communication devices and the electrical network. The plurality of nodes may be spaced apart by the plurality of the cords to define the plurality of air gaps. The plurality of cords may be expandable to receive a portion of the wearer and contractible to position the wearable structure on the portion of the wearer. The plurality of cords may resiliently expand and contract to obtain a close fit between the wearable structure and the skin. The plurality of nodes and the plurality of cords may be 3D printed from the biocompatible material in one or more stages so that the electrical network is contained in the plurality of nodes.

A portion of the structure may be contractible to press the skin contacting surface into the skin with a normal force that establishes a friction fit between the skin contact surfaces and the skin. The skin contacting surface may be curved to increase a contact area with the skin. The skin contacting surface may be operable to maintain a minimum coefficient of friction with the skin of the wearer. The skin contact surface may comprise one of a localized geometric feature or a biocompatible adhesive operable to maintain the minimum coefficient of friction. The wearable structure may comprise a cylindrical shape extending along a longitudinal axis. The wearable structure may be wrapped around a portion of the wearer about the longitudinal axis to define the cylindrical shape. The wearable structure may comprise a first end with a first engagement structure at a first end, a second end with a second engagement structure at a second end, and the first engagement structure may be engageable with the second engagement structure to wrap the structure around the portion of the wearer.

Each device of the plurality of data communication devices may comprise a housing removably engageable with the wearable structure and a conductor removably engagable with the electrical network when the housing is removably engaged with the wearable structure. One or more devices of the plurality of data communication devices may comprise: at least one sensor; and one haptic generator of the plurality of haptic generators. The at least one sensor may comprise a physiological sensor operable to output a first portion of the contextual data. The at least one sensor may comprise an environmental sensor operable to output a second portion of the contextual data. The physiological sensor may be oriented toward the skin of the wearer. The environmental sensor may be oriented away from the skin of the wearer.

One or more devices of the plurality of data communication devices may comprise a touchscreen operable to receive inputs from the wearer. The one or more devices of the plurality of data communication devices may comprise: at least one sensor; and one haptic generator of the plurality of haptic generators. The touchscreen may comprise an electronic visual display and a contact sensing surface. The electronic visual display may be operable to display an icon and the contact sensing surface may be operable to detect a gesture applied to the touchscreen by a finger of the wearer. The contact sensing surface may comprise a fingerprint sensor operable to detect a fingerprint of the finger when applying the gesture. The plurality of data communication devices may comprise a location sensor operable to determine a location of the apparatus when the fingerprint is detected with the fingerprint sensor. The plurality of data communication devices may comprise a camera operable to capture a picture of the wearer when the fingerprint is detected with the fingerprint sensor. The control system may operable to confirm an identify of the wearer based on one of the fingerprint, the location, and the picture.

Related apparatus, kits, methods, and systems also are described.

DESCRIPTION OF THE DRAWINGS

The accompanying drawings are incorporated in and constitute a part of this specification. These drawings illustrate exemplary aspects of the present disclosure that, together with the written descriptions provided herein, serve to explain the principles of this disclosure.

DETAILED DESCRIPTION

Figure 1:
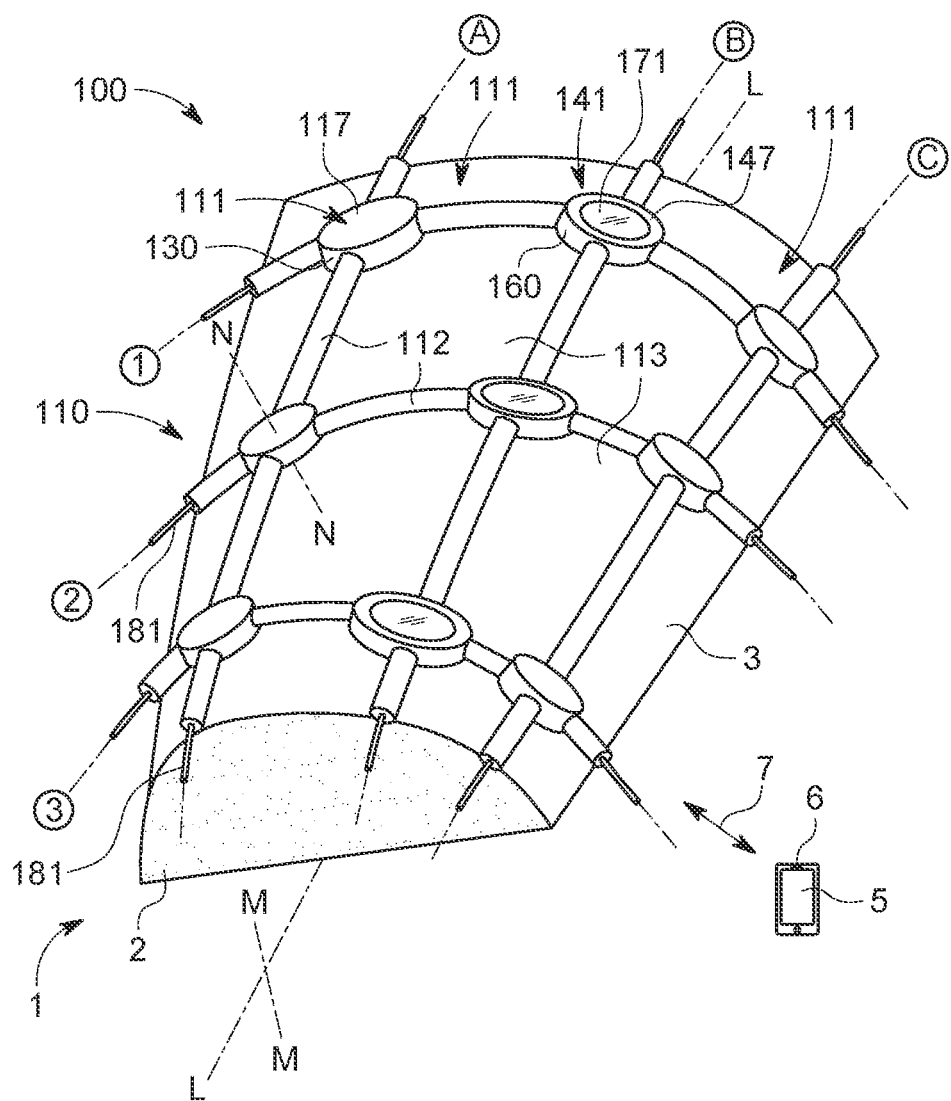
FIG. 1 depicts an exemplary wearable data communication apparatus.

Aspects of the present disclosure are not limited to the exemplary structural details and component arrangements described in this description and shown in the accompanying drawings. Many aspects of this disclosure may be applicable to other aspects and/or capable of being practiced or carried out in various variants of use, including the examples described herein. Any example or variation may be claimed.

Throughout the written descriptions, specific details are set forth in order to provide a more thorough understanding to persons of ordinary skill in the art. For convenience and ease of description, some well-known elements and methods are described conceptually to avoid unnecessarily obscuring the focus of this disclosure. In this regard, the written descriptions and accompanying drawings should be broadly interpreted as illustrative rather than restrictive, enabling rather than limiting.

Exemplary aspects of this disclosure reference wearable data communication apparatus, kits, methods, and systems. Some aspects are described with reference to particular structures (e.g., a lattice structure) made with particular materials (e.g., medical grade silicone) using a particular manufacturing method (e.g., 3D printing) into a particular shape (e.g., a cylindrical sleeve) wearable on a particular portion (e.g., a forearm) of a particular user (e.g., a living animal or human). Unless claimed, these exemplary aspects are provided for convenience and not intended to be limiting.

Several different reference axes are described, including a longitudinal axis and a lateral axis. Relevant arrangements may be described in relation to the different reference axes. For example, the longitudinal axis may be non-parallel with the lateral axis in some perspectives, meaning that one axis extends across the other. Relative terms such as "long" and "elongated" may describe any aspect having a length along one reference axis (e.g., the longitudinal axis) that is longer in relation to a width along a non-parallel reference axis (e.g., the lateral axis). Anatomical terms such as "anterior" and "posterior," "medial" and "lateral," and "proximal" and "distal" may be used to describe some structures in relation to a reference axis. For example, the longitudinal axis may be parallel to a bone structure of a user (e.g., a lower arm) and extend between a proximal end of the bone structure (e.g., an elbow) and a distal end of the bone structure (e.g., a hand), making it a proximal-distal axis. Movements and forces may be similarly described in relation to any reference axis. As before, the different reference axes and any terms associated therewith are provided for convenience and not intended to limit this disclosure unless claimed.

As used herein, inclusive terms such as "comprises," "comprising," "includes," "including," and variations thereof, are intended to cover a non-exclusive inclusion, such that any wearable data communication apparatus, kits, methods, system, or element thereof that is described herein as comprising an exemplary list of elements does not include only those elements but may include other elements not expressly listed and/or inherent thereto. Unless stated otherwise, the term "exemplary" is used in the sense of "example," rather than "ideal," and does not limit this disclosure to any particular embodiment. Various terms of approximation may be used in this disclosure, including "approximately" and "generally." Unless stated otherwise, approximately means within 10% of a stated number or outcome and generally means "within most cases" or greater than 50% chance.

General aspects of this disclosure may comprise a plurality of nodes interconnected with a plurality of cords to define a structure with a 3D geometry wearable on a user 1, in which: (1) the plurality of nodes may contain a plurality of data communication devices; (2) the structure may be worn for a period of time to augment a performance of user 1 by positioning the data communication devices relative to the skin, eyes, and/or environment of user 1; and/or (3) skin contacting surfaces of the structure may maintain a position of the devices on user 1 during the period of time.

The nodes, cords, and structure may be formed or printed with a biocompatible material (e.g., such as silicone) that is wearable on a limb 2 of user 1 for periods of time. Each node may contain an electronic device that is positionable on or adjacent the skin by the structure when worn on limb 2. The 3D geometry of the structure may define a generally cylindrical shape extending along an upper or lower limb axis of limb 2. The biocompatible material may allow the structure to undergo a repeatable set of deformation and flexural stresses when user 1 dons, wears, and removes the structure. For example, when user 1 dons the structure, interior portions of the cords may expand to receive limb 2, allowing the structure to be fit over the hand; and then contract around limb 2, allowing the structure to obtain a close fit with limb 2 and exert compressive forces that press its skin contacting surfaces against the skin of limb 2, causing frictional forces that maintain a position of the structure and its devices.

Particular aspects of this disclosure are now described with reference to an exemplary data communication apparatus 100 that is wearable on limb 2 of user 1 to augment their performance by maintaining one or more data feedback loops with user 1. As shown in FIG. 1, data communication apparatus 100 may be operable with an application 5 of a computing device 6 over a wireless network 7. Data communication apparatus 100 may be adapted to position of a plurality of electronic devices positioned on or adjacent skin 3 to limb 2 for a period of time, even if limb 2 is flexing and/or moving. The plurality of electronic devices may be operable with application 5 to maintain the one or more data feedback loops with user 1 during the period of time.

Different types of electronic devices may be positioned on limb 2 with data communication apparatus 100 and operable with application 5 to collect different types of data from and/or communicate different types of data to user 1. The plurality of electronic devices may comprise any combination of output devices, sensors, processors, power supplies, and like technologies, including the examples now described.

As shown in FIGS. 1 and/or 2, data communication apparatus 100 may comprise a structure 110, a plurality of data communication devices 130, a plurality of data communication devices 160, and an electrical network 180. Data communication apparatus 100 may utilize these elements to maintain one or more data feedback loops or "Haptic Loops™" with user 1 during a period of time by continuously: (i) sending contextual data to and receiving control signals from application 5 of user device 6 over wireless network 7; and (ii) outputting haptic energies to nerves associated with skin 3 responsive to the control signals. The haptic loops may enhance user 1's reactivity to data. For example, each haptic loop maintained with user 1 during the period of time may provide a non-invasive way for user 1 to augment their behavior responsive to the contextual data by taking actions based on the energies output to skin 3.

Figure 2:
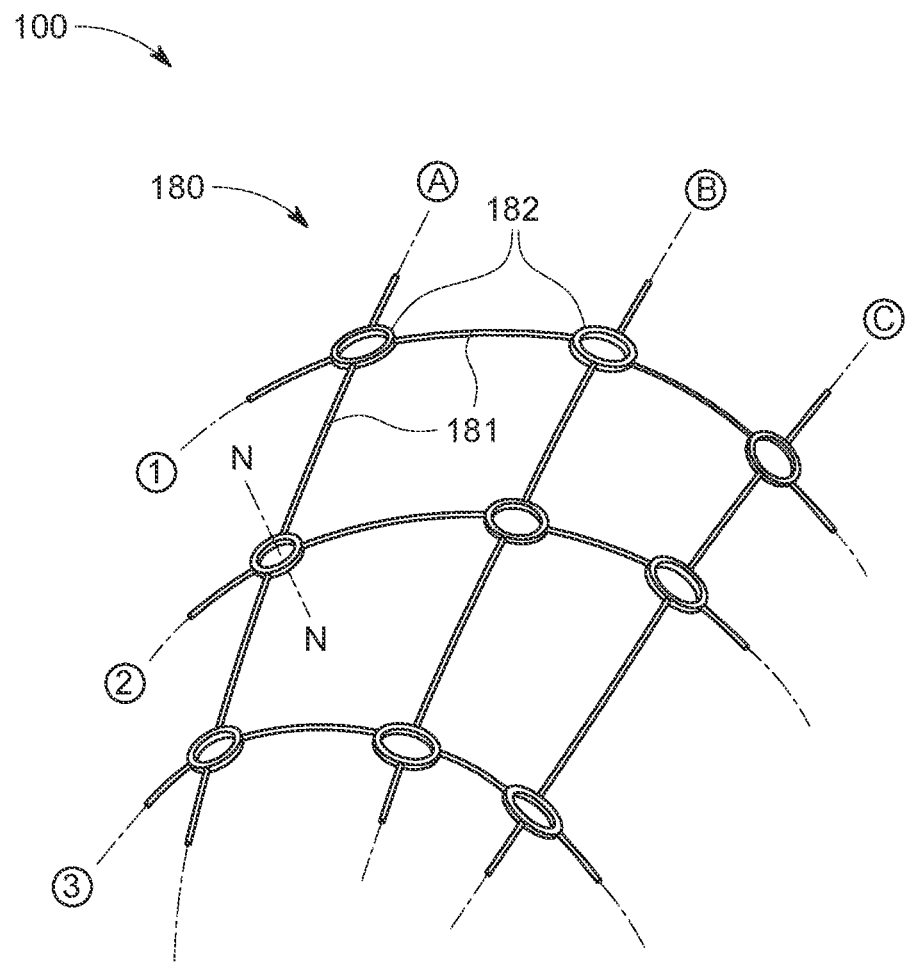
FIG. 2 depicts an exemplary electrical network of the FIG. 1 apparatus.

As shown in FIG. 1, structure 110 may comprise a plurality of structurally interconnected elements defining a plurality of skin contacting surfaces that are positionable against skin 3 of user 1 for a period of time, such a typical work shift (e.g., 6 to 12+ hours). The plurality of structurally interconnected elements may be shaped to contain plurality of data communication devices 130, plurality of data communication devices 160, and electrical network 180. As shown in FIG. 2 and described further below, electrical network 180 may comprise a plurality of interconnected conductive materials spanning between plurality of devices 130, 160 to define a power and data communication network contained in structure 110. Structure 110 and/or electrical network 180 may comprise elastic elements or properties causing structure 110 to perform like an elastic mesh or a length of nylon stocking. As shown in FIG. 1, portions of structure 110 may resiliently expand and contract to obtain a close fit between structure 110 and skin 3 and maintain a position of structure 110 on skin 3.

As shown in FIG. 1, structure 110 may comprise a plurality of nodes 111 and/or a plurality of nodes 141, a plurality of cords 112, and a plurality of air gaps 113. Plurality of nodes 111, 141 may be interconnected with plurality of cords 112 to define plurality of air gaps 113 between plurality of nodes 111, 141. Each node of plurality of nodes 111, 141 may be interconnected to and spaced apart from each another node of nodes 111, 141 by one or more cords of plurality of cords 112 to define a swatch of fabric-like material that, similar to a swatch of traditional cloth fabric, may be representative of a larger whole of a wearable accessory or item.

Figure 3:
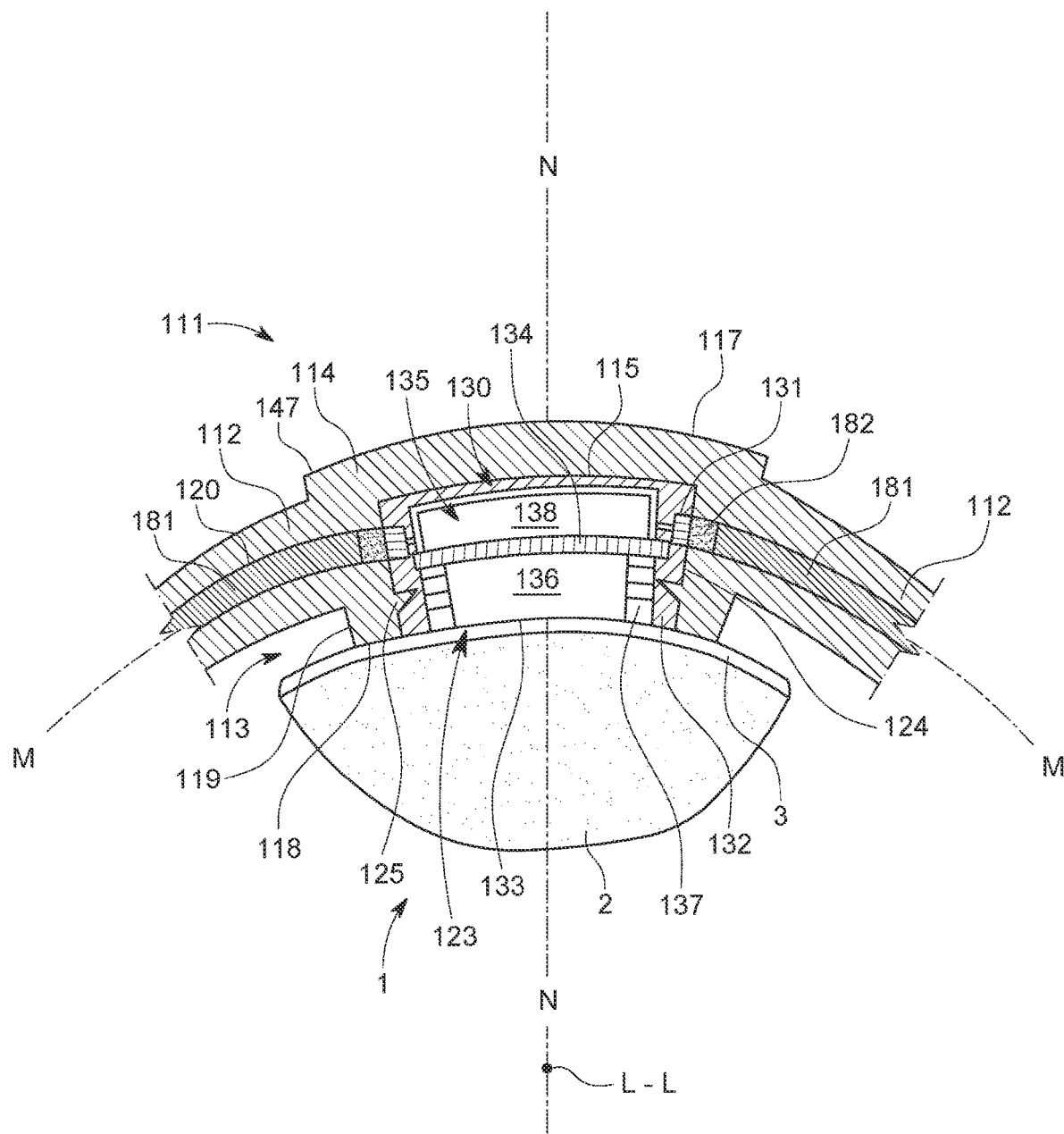
FIG. 3 depicts an exemplary electrical device of the FIG. 1 apparatus.
Figure 4:
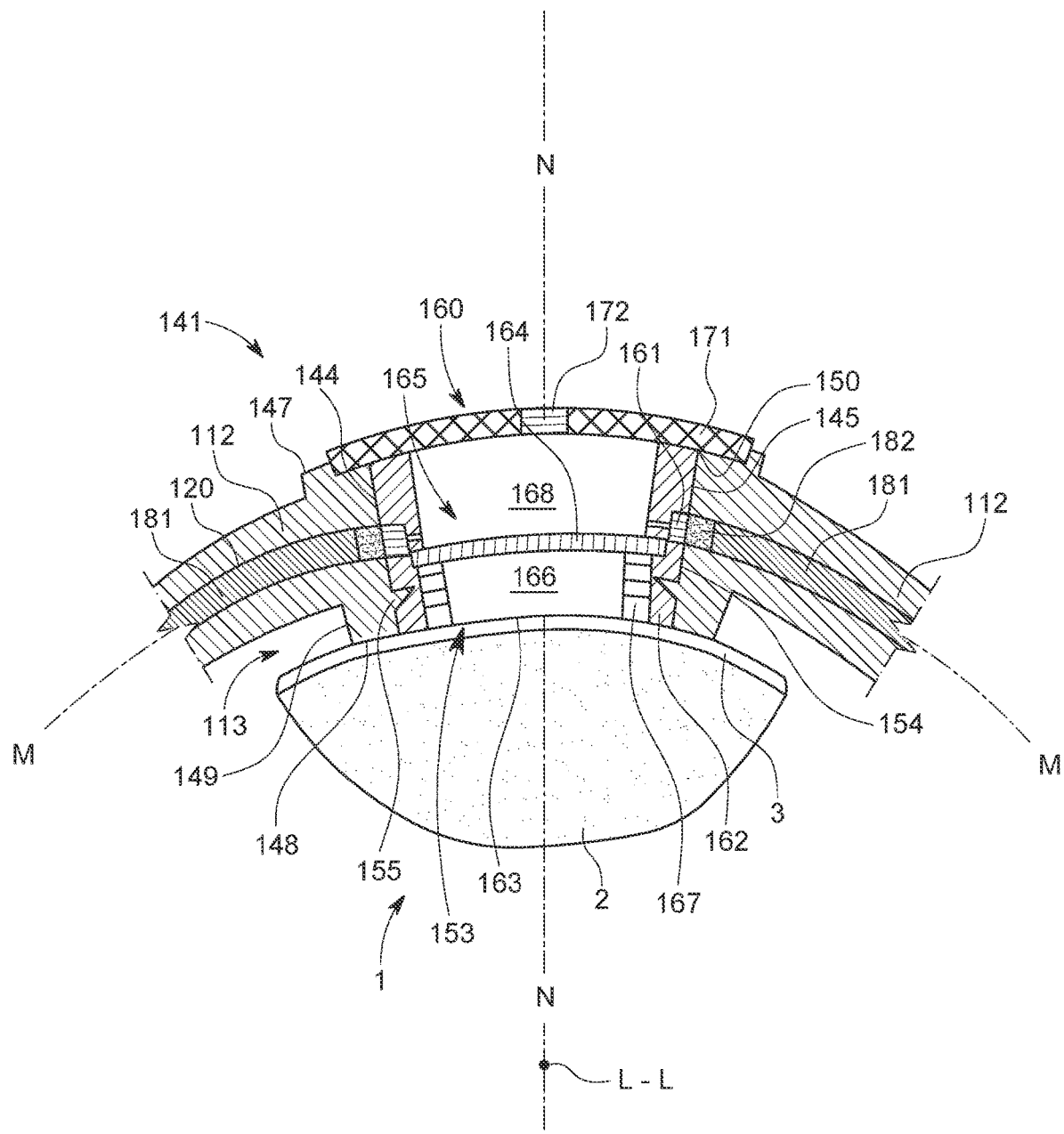
FIG. 4 depicts another exemplary electrical device of the FIG. 1 apparatus.

As shown in FIG. 2, electrical network 180 may comprise a conductor 181 contained in each cord 112 and a conductive ring 182 contained in each node 111, 141. Plurality of nodes 111 may contain plurality of data communication devices 130 and comprise skin facing surfaces operable with skin 3 to maintain their position on user 1. Plurality of nodes 141 may contain plurality of data communication devices 160 and similarly comprise skin facing surfaces operable with skin 3 to maintain their position on user 1. As shown in FIGS. 3, 4, each data communication device 130, 160 may (e.g., via electrical network 180) be electrically interconnected with each other communication device 130, 160 when contained in plurality of nodes 111, 141.

An exemplary cross-section of one node 111 is shown in FIG. 3 as comprising a body 114 and a bay 115. Body 114 may be operable with cords 112 to maintain a generally fixed position of structure 110 when worn on limb 2. In this position, plurality of data communication devices 130 may be rotationally and/or translationally fixed relative to a longitudinal axis L-L of limb 2, such as a lower arm axis. As shown in FIG. 3, body 114 may comprise a 3D shape defining an outward facing surface 117, a skin contacting surface 118, and a body sidewall 119. The 3D shape may be curved to limit deformations of body 114 and bay 115. For example, the 3D shape may comprise a cylindrical shape like that shown in FIG. 1. Outward facing surface 117 may be smooth and unadorned for simplicity. As shown in FIG. 3, outward facing-surface surface 117 may be spaced apart from skin contacting surface 118 a lateral axis M-M of limb 2 that is non-parallel with longitudinal axis L-L. As shown in FIGS. 1 and 3, lateral axis M-M may be parallel with a node axis N-N of node 111 that is perpendicular with skin 3 when structure 110 is worn on limb 2.

Skin contacting surface 118 may be curved to match a curved shape of limb 2 and/or skin 3. As shown in FIG. 3, skin contacting surface 118 may comprise material characteristics, geometrical features, and/or surface treatments operable to maintain a minimum coefficient of friction with skin 3 in a variety of usage conditions, such as when structure 110 is worn dry, exposed to heat and/or perspiration, and when partially or fully submerged in water. Skin contacting surface 118 may, for example, comprise a medical grade silicone having a minimum coefficient of friction with skin 3 of approximately (0.61+/−0.21)[1]. To enhance its frictional engagement with skin 3, skin contacting surface 118 may comprise localized geometrical features that intentionally roughen and/or otherwise increase its surface area. Portions of the skin contacting surface 118 may be covered with a mild biocompatible adhesive or tacky material. A size and/or shape of skin contacting surface 118 may be maximized, increased, and/or otherwise modified to increase a probability that at least a portion of surface 118 will be generally and consistently maintained against skin 3 during vigorous movements of limb 2, such as when structure 110 is worn while playing sports. As a further example, skin contacting surface 118 may comprise a flexible concave shape (e.g., like a suction cup) that may be pressed against skin 3 (e.g., by nodes 112) to form a sealing edge therewith.

As shown in FIG. 3, body sidewall 119 may be engaged to one or more cords 112 and adapted to transfer forces therebetween when structure 110 is worn. Each body sidewall 119 of each node 111 may be structurally interconnected to at least one other body sidewall 119 of another node 111 by at least one cord 112 extending therebetween. Cord 112 may comprise a sidewall defining generally circular cross-sectional shape with an interior lumen 120 extending between and through two different body sidewalls 119 of two different nodes 111. Interior lumens 120 may extend completely or partially through sidewalls 119. Opposing ends of cord 112 may be engaged to two different body sidewalls 119 so that at least a central portion of cord 112 between sidewalls 119 may elastically expand and contract (e.g., like a spring) when user 1 dons, wears, and removes structure 110. The material characteristics and/or thicknesses of cords 112 and sidewalls 119 may define elastic properties of each cord 112, such as a spring constant of its central portion and/or a maximum amount of elastic force applicable to skin contacting surface 118 therewith.

Each bay 115 may contain one data communication device 130 and maintain its position relative to skin 3. As shown in FIG. 3, bay 115 may comprise a skin facing opening 123 and interior surfaces 124. Skin facing opening 123 may comprise a generally circular shape extending through skin contacting surface 118, giving it an annular shape. Interior surfaces 124 may be operable with data communication device 130 to maintain its position relative to skin 3 when structure 110 is worn on limb 2, such as a vertical position on or adjacent skin 3 along node axis N-N. Interior surfaces 124 may comprise a generally semi-spherical shape that extends into body 114 along node axis N-N from skin facing opening 123 and may be described as a surface of revolution formed about axis N-N. Data communication device 130 may be inserted into bay 115 along node axis N-N. As shown in FIG. 3, interior surfaces 124 may comprise a resilient lip 125 with a generally triangular shape extending outwardly toward node axis N-N. The generally triangular shape of resilient lip 125 may elastically deform to admit data communication device 130 into bay 115 and expand to maintain data communication device 130 in bay 115.

A cross-section of one exemplary data communication device 130 is shown in FIG. 3 as comprising an electrical contact 131, a housing 132, a skin facing surface 133, an interior support 134, and operational components 135. Electrical contact 131 may comprise a conductive ring that is mounted on housing 132 and comprises a conductive surface flush with exterior surfaces of housing 132. As shown in FIG. 3, housing 132 may be inserted into bay 115 along node axis N-N so that the conductive surface of electrical contact 131 is electrically connected to electrical network 180 and thus operable to route data and power to operational components 135. Housing 132 may comprise a rigid biocompatible material (e.g., ABS, PLA, PEEK, etc.). As shown in FIG. 3, exterior surfaces of housing 132 may define a generally semi-spherical shape corresponding to the shape of interior surfaces 124 of bay 115. Skin facing surface 133 may be spaced apart from skin 3. As shown in FIG. 3, an edge portion of housing 132 may interact with an interior surface of resilient lip 125 to contain data communication device 130 in bay 115, establish a seal that prevents moisture from entering bay 115, and/or maintain the electrical connection between electrical contact 131 and the electrical contact of electrical network 180.

Interior support 134 may be located in housing 132 and sized to contain operational components 135. For example, interior support 134 may comprise a printed circuit board (or "PCB") with edges that are engageable with interior surfaces of housing 132 to position operational components 135 in housing 132. As shown in FIG. 3, the edges of interior support 134 may be located in an annular recess formed into housing 132 to define a proximal cavity of housing 132 positioned below interior support 134 and a distal cavity of housing 132 positioned above interior support 134. Housing 132, skin facing surface 133, interior support 134, and/or operational components 135 may comprise seals and/or sealing elements that prevent moisture from entering the proximal and distal cavities of housing 132 and/or otherwise interfering with operational components 135 when structure 110 is worn.

As described herein, data communication apparatus 100 may comprise different types of data communication devices 130, each of which may be positioned by structure 110 on a different portion of limb 2 when structure 110 is worn. Some aspects of each different data communication device 130 may be similar, such as electrical contact 131, housing 132, skin facing surface 133, and/or interior support 134; whereas other aspects of each device 130 may be similar or different, such operational components 135. As shown in FIG. 3, operational components 135 may comprise any combination of physiological sensors, haptic devices, and/or input devices. Particular combination(s) of data communication devices 130 may be selected by user 1 for use with a generic structure 110, allowing the capabilities of data communication apparatus 100 to be mass customized without having to redesign structure 110.

Some data communication devices 130 may communicate non-visually with user 1 by outputting one or more different types of haptic energy to nerves associated with skin 3 when structure 110 is worn. As shown in FIG. 3, operational components 135 may comprise a haptic energy generator 136, a sensor 137, and a controller 138. Haptic energy generator 136 may be mounted to interior support 134 and located in the proximal cavity of housing 132. For example, haptic energy generator 136 may comprise any haptic energy generation technologies including: (i) any type of single energy haptic communication technologies, such as a vibration generator; and (ii) any type of multi-energy haptic communication technologies, including those described in U.S. Pat. No. 10,959,674, issued Mar. 30, 2021, and U.S. Provisional Patent Application No. 63/019,302, filed May 2, 2020, the entireties of which are hereby incorporated by reference into this disclosure.

As shown in FIG. 3, haptic energy generator 136 may comprise electromagnetic components mounted to a mounting pad on the proximal surface of interior support 134. The electromagnetic components may comprise any technologies operable to generate the one or more different types of haptic energies, including any type of mass mover operable to cause pressures and/or vibrations, and any type of electrical generator, heat generator, pressure generator, vibration generator, and the like. Working portions of the electromagnetic components may extend proximally toward skin 3 along node axis N-N so that they are located on or adjacent skin 3 (e.g., beyond skin facing surface 133) when structure 110 is worn. Interior support 134 may maintain a distance between the working portions of haptic energy generator 136 and skin 3. As shown in FIG. 3, interior support 134 may comprise internal beam elements spanning between its edges to maintain a contact between the working portions and skin 3 and/or help transfer forces between housing 132 and skin 3.

As shown in FIG. 3, sensor 137 may comprise sensory components mounted on a mounting pad on the lower surface of interior support 134 and thus located in the proximal cavity of housing 132. The sensory components may comprise any technologies operable with controller 138 to capture contextual data associated with user 1, including any physiological measures of user 1 that are detectable from a position on or adjacent skin 3, including blood pressure, body temperature, heart rate, perspiration rate, toxicity levels, and the like. Working portions of sensor 137 may extend toward skin 3 along node axis N-N so that they are located on or adjacent skin 3 (e.g., beyond skin facing surface 133) when structure 110 is worn. Interior support 134 may similarly maintain a distance between the working portions of sensor 137 and skin 3 to maintain a contact between the working portions and skin 3.

Controller 138 may comprise data processing components mounted on a mounting pad on the distal surface of interior support 134 and thus located in the distal cavity of housing 132. The data processing components may comprise any combination of one or more processors, memory elements, and transceivers, operable to store an execute a firmware of data communication apparatus 100. Each controller 138 may comprise its own power source (e.g., a rechargeable lithium-ion battery) and be electrically connected to electrical contact 131, making it operable to receive data and power from electrical network 180. As shown in FIG. 3, the data processing components of controller 138 may be located on a distal surface of interior support 134, in the distal cavity of housing 132, so that they are well positioned to reject heat into node 111 and avoid interference with the haptic energies output from energy generator 136.

An exemplary cross-section of one node 141 is shown in FIG. 4 as comprising a body 144 and a bay 145. Aspects of body 144 and bay 145 are similar to aspects of body 114 and bay 115 of node 111 and may use similar element numbers; whereas other aspects of body 144 and bay 145 are modified to accommodate data communication device 160 and may introduce new element numbers. Body 144 may be similarly operable with cords 112 to maintain a generally fixed position of structure 110 when worn on limb 2. As shown in FIG. 4, body 144 may comprise a 3D shape geometry defining an outward facing surface 147, a skin contacting surface 148, and a body sidewall 149. The 3D shape may be curved to limit deformations of body 144 and bay 145. For example, the 3D shape may comprise a cylindrical shape like that shown in FIG. 1. As shown in FIG. 4, outward facing surface 117 may comprise an outward facing opening extending therethrough and a recessed portion surrounding outward facing opening 150. As shown in FIG. 4, outward facing surface 147 may be spaced apart from skin contacting surface 148 along lateral axis M-M and/or node axis N-N. As shown in FIG. 4, skin contacting surface 148 and body sidewall 149 may be similar to body sidewall 119 described above. Accordingly, as shown in FIG. 1, each body sidewall 119, 149 of each node 111, 141 may be structurally interconnected to another body sidewall 119, 149 of another node 111, 141 by at least one cord 112 extending therebetween; and each cord 112 may comprise a sidewall defining generally circular cross-sectional shape with interior lumen 120 extending between and through two different body sidewalls 119, 149.

Each bay 145 may contain one data communication device 160 and maintain its position relative to skin 3. As shown in FIG. 4, bay 145 may comprise a skin facing opening 153 and interior surfaces 154. Skin facing opening 153 may comprise a generally circular shape extending through skin contacting surface 148, giving it an annular shape like that of skin facing opening 123. Interior surfaces 154, like interior surfaces 124, may be operable with data communication device 160 to maintain its position relative to skin 3 when structure 110 is worn on limb 2, such as a vertical position on or adjacent skin 3 along node axis N-N. In contrast to above, interior surfaces 154 may comprise a generally cylindrical shape extending into body 144 along node axis N-N between outward facing opening 150 and skin facing opening 153. The shape of interior surfaces 154 also be described as a surface of revolution about node axis N-N. Data communication device 160 may be inserted into bay 145 in a direction along node axis N-N. As shown in FIG. 4, interior surfaces 154 may comprise a resilient lip 155 with a generally triangular shape extending outwardly toward node axis N-N. As above, the generally triangular shape of resilient lip 155 may elastically deform to admit data communication device 160 into bay 145 and expand to maintain data communication device 160 in bay 145.

A cross-section of one exemplary data communication device 160 is shown in FIG. 4 as comprising an electrical contact 161, a housing 162, a skin facing surface 163, an interior support 164, and operational components 165. Electrical contact 161 may comprise a conductive ring that is mounted on housing 162 and comprises a conductive surface flush with exterior surfaces of housing 162. As shown in FIG. 4, housing 162 may be inserted into bay 145 along node axis N-N so that the conductive surface of electrical contact 161 is electrically connected to electrical network 180 and thus operable to route data and power to operational components 165. Housing 162 may comprise a rigid biocompatible material (e.g., ABS, PLA, PEEK, etc.). As shown in FIG. 4, exterior surfaces of housing 162 may define a generally semi-spherical shape corresponding to the shape of interior surfaces 154 of bay 145. Skin facing surface 153 may be spaced apart from skin 3. As shown in FIG. 4, an edge portion of housing 162 may interact with an interior surface of resilient lip 155 to contain data communication device 160 in bay 145, establish a seal that prevents moisture from entering bay 145, and/or maintain the electrical connection between electrical contact 161 and the electrical contact of electrical network 180.

Interior support 164 may be located in housing 162 and sized to contain operational components 165. For example, interior support 164 may comprise a printed circuit board (or "PCB") with edges that are engageable with interior surfaces of housing 162 to position operational components 165 in housing 162. As shown in FIG. 4, edges of interior support 164 may be located in an annular recess formed into housing 162 to define a proximal cavity of housing 162 located below interior support 164 and a distal cavity of housing 162 locate above interior support 164. Housing 162, skin facing surface 163, interior support 164, and/or operational components 165 may comprise seals and/or sealing elements that prevent moisture from entering the distal and proximal cavities of housing 162 and/or otherwise interfering with operational components 165 when structure 110 is worn.

As described herein, data communication apparatus 100 may similarly comprise different data communication devices 160, each of which may be positioned by structure 110 on a different portion of limb 2 when structure 110 is worn. As above, some aspects of each communication device 160 may be similar, such as electrical contact 161, skin facing surface 163, and interior support 164; whereas other aspects of each device 160 may be similar or different, such as housing 162 and operational components 165. As shown in FIG. 4, operational components 165 may comprise any combination of physiological sensors, haptic devices, and/or input devices. As before, particular combination(s) of data communication devices 160 may be selected by user 1 for use with a generic structure 110, providing opportunities for mass customization.

Like data communication devices 130, some data communication devices 160 may communicate non-visually with user 1 by outputting one or more different haptic energy types to nerves associated with skin 3 when structure 110 is worn. As shown in FIG. 4, operational components 165 may comprise elements like those of operational components 135 described above, including a haptic energy generator 166, a sensor 167, and controller 168. Haptic energy generator 166 and sensor 167 may be similar to haptic energy generator 136 and sensor 137 described above. For example, haptic energy generator 166 and sensor 167 may be similarly mounted to interior support 164 and located in the proximal cavity of housing 122. Because of these similarities, the non-visual communication capabilities of data communication devices 160 may be similar to the non-visual communication capabilities of data communication devices 130, making devices 130, 160 interchangeably operable to communicate with the brain of user 1 using their nerves, such as the associated with skin 3.

Controller 168 may comprise data processing components mounted on a mounting pad on the distal surface of interior support 164 and thus located in the distal cavity of housing 162. The data processing components may comprise any processor(s), memory element(s), and/or transceiver(s), operable to store an execute the firmware of data communication apparatus 100. For controller 168, the data processing components may comprise additional image and/or video processing components, making them larger and more powerful than the data processing components of controller 138. Each controller 168, like each controller 138, may comprise its own power source (e.g., a rechargeable lithium-ion battery) and be electrically connected to electrical contact 161, making it operable to receive data and power from electrical network 180. As shown in FIG. 4, the data processing elements of controller 168 may be located on a distal surface of interior support 164, in the distal cavity of housing 162, so that they are better positioned to reject heat to node 141 and avoid interference with the haptic energies output from haptic energy generator 166.

Data communication device 160 may comprise additional communication capabilities enabled by operational components 165, which may comprise additional communication and/or sensing technologies oriented outwardly from skin 3, toward eyes of user 1 and/or their environment. As shown in FIG. 4, an outward facing portion of housing 162 may extend through outward facing opening 150 of node 141 and comprise a touchscreen 171 and a sensor 172. Housing 162 and may slid into the generally cylindrical shape of interior surfaces 154 in a proximal direction so that touchscreen 171 and sensor 172 are proximate outward facing surface 147 of node 141. An interface surface of touchscreen 171 may extend outwardly from housing 162 and be seated in the recessed portion of node 141 surrounding opening 150, making it accessible to the eyes and digits of user 1. A remainder of touchscreen 171 may be contained in the distal cavity of housing 162.

Touchscreen 171 may comprise interactive components operable with controller 168 to collect input data from user 1 and/or their environment and communicate visually with the eyes and/or skin of user 1. As shown in FIG. 4, the interactive components of touchscreen 171 may comprise an electronic visual display and a contact sensing surface. The electronic visual display may comprise a first layer or portion of touchscreen 171 comprising any display technologies, such as LCD, OLED, and the like. As shown in FIGS. 1 and 3, a diameter of the electronic visual display may be approximately 3-10 mm, with the minimum size being determined based on user 1's ability to recognize the visual data output therewith, making the display small, yet large enough to output visual data to user 1, such as shapes and colors. For example, the electronic visual display may comprise a generally circular array of pixels operable with controller 168 to output visual data comprising indicia (e.g., a logo) of an action caused by contacting touchscreen 171 (e.g., a purchase), making it operable like a labeled button operable to perform the action.

The contact sensing surface may comprise a second layer or portion of touchscreen 171 comprising any contact sensing technologies, including any combination of one or more contact sensors, such as projected capacitive sensors, analog resistive sensors, surface capacitive sensors, surface acoustic wave sensors, infrared sensors, camera-based optical sensors, liquid crystal display in-cell sensors, bending wave sensors, force sensors, planar scatter detection sensors, vision-based sensors, and/or electromagnetic resonance sensors. As shown in FIG. 4, touchscreen 171 may be contained in the perimeter of outward facing opening 150, and slightly offset from outward facing surface 147 so that user 1 may place a digit on and/or slide the digit across the contact sensing surface 174 without interference from outward facing surface 147. Much like the electronic visual display, the contact sensing surface may be small, yet large enough to capture inputs from user 1, including a gesture applied to touchscreen 171 by a digit of user 1 (e.g., an on/off tap, a hold, a directional swipe, etc.) and a fingerprint of the digit (e.g., as a part of a fingerprint scanning hold gesture). The contact sensing surface may be part of the electronic visual display. For example, the contact sensing surface may comprise an array of contact sensors that are embedded in the generally circular array of pixels noted above and similarly operable with controller 168 to capture the inputs and/or a fingerprint associated therewith.

As shown in FIG. 4, sensor 172 (or "environmental sensor 172") may comprise sensory components that are mounted on interior support 164 and located in the distal cavity of housing 162. The sensory components may comprise any technologies operable with controller 168 to capture additional contextual data associated with user 1 and/or their environment, including any chemical, electrical, physical, and/or physiological measures of user 1 and/or their environment. As shown in FIG. 4, portions of sensor 172 may part of and/or positioned relative to touchscreen 171. For example, sensor 172 may comprise: one or more optical sensors, photo-sensing transistors, camera elements, and/or capacitor circuits embedded with the electronic visual display of touchscreen 171 (e.g., into some or all of an LCD's pixels, such as in the TFT backplate) and/or the contact sensing surface of touchscreen 171 (e.g., mounted to proximal side of surface 174). Any type of sensor may be similarly incorporated to generate the contextual data. For example, sensor 172 also may comprise: any geolocating technologies, such as those utilizing GPS signals; and/or any motion sensing technologies operable to identify a specific force, angular rate, and/or orientation of limb 2, such as an inertial measurement unit.

Electrical network 180 may comprise a plurality of interconnected conductive materials defining an electrical network that is contained in structure 110 and operable to transmit power and data between data communication devices 130, 160. As shown in FIG. 2, electrical network 180 may comprise a plurality of conductors 181 and a plurality of conductive rings 182. Conductors 181 and conductive rings 182 may comprise metallic wires and/or electrically conductive filaments (e.g., graphene PLA filament) operable to transmit data and power between two different data communication devices 130, 160 contained in two different nodes 111, 141. Any type of conductive elements may be utilized, any of which may include conductors that are layered and/or bundled or braided together. As shown in FIGS. 3 and 4, conductor 181 may extend through interior lumen 120 and surrounded by cord 112. Conductive ring 182 may be located in an interior portion of body 114, 144 and surrounded by node 111, 141. An end portion of conductor 181 may extend through body sidewall 119, 149 into the interior portion of body 114, 144, electrically connected to conductive ring 182 therein, and thus also surrounded by body 114.

Conductive ring 182 may have a connection surface engaged with the interior portion of body 114, 144 and a contact surface flush with interior surfaces 124, 154 of bay 115, 145. As shown in FIGS. 3 and 4, the connection surface of ring 182 may be located in an annular recess formed in interior surfaces 124, 154 of bay 115, 145. The connection surface of conductive ring 182 in node 111, 141 may be engaged (e.g., soldered or formed integral with) with the end portions of each conductor 181 extending through body sidewall 119, 149. Many different conductors 181 may be electrically connected to the connection surface of each conductive ring 182 in each node 111, 141, one for each data communication device 130, 160 in each adjacent node 111, 141. Because medical grade silicone is an electrical insulator, each of nodes 111, nodes 141, cords 112, and electrical network 180 may thus be operable to provide parallel connections for transmitting data and power between data communication devices 130, 160 in nodes 111, 141.

Control system 190 may comprise a distributed computing system with individual processing resources that are located at different locations and yet in generally constant data communication with one another. In this way, the individual processing resources may communicate with one another to achieve a common goal, such as maintaining one or more data feedback loops with user 1. As shown in FIG. 1, controllers 138, 168 may be electrically interconnected to each other via electrical network 180 and at least one controller 138, 168 may comprise a transceiver in data communication with application 5 of user device 6. Controllers 138, 168 may thus serve as individual processing resources of control system 190 that are located at different locations on user 1, in data communication with one another and application 5 over electrical network 180, and thus operable with firmware of control system 190 to maintain the one or more data feedback loops. Control system 190 may incorporate the capabilities of any individual processing resources in this manner, including user device 6 and any other resources in data communication therewith, including any cloud-based resources. The firmware of control system 190 may be described as a distributed program including lines of code that are stored on the memories of controllers 138, 168 and executable by the data processing components of controllers 138, 168 to: (i) send data to and receive control signals from application 5 of user device 6; and (ii) transmit control signals and power to data communication devices 130, 160. As shown in FIG. 1 and described herein, the processing power of control system 190 may thus be proportionate to the processing power of each controller 138, 168, user device 6, and any other resource in data communication therewith.

Manufacturing aspects of data communication apparatus 100 are now described. As shown in FIGS. 1-4, data communication apparatus 100 may be mass-customized for user 1, meaning that its dimensions may be determined based on an actual or estimated size limb 2 and/or skin 3. Limb 2 may extend along longitudinal axis L-L between a proximal end and a distal end to define a generally cylindrical shape of skin 3 with different diameters at different locations along axis L-L. As shown in FIG. 1, limb 2 may comprise a human forearm extending along longitudinal axis L-L between a hand at lower-left (not shown) and an elbow at upper-right (not shown) to define a generally cylindrical shape tapering from a smaller diameter at the hand (e.g., at row 3 of FIG. 1) to a series of generally increasing larger rows toward the elbow (e.g., at rows 1, 2 of FIG. 1. The size of each diameter of each row may be provided by user 1 and utilized to determine a geometrical basis for defining the dimensions and curvatures of structure 110. For example, user 1 may perform a procurement method 200 comprising: (i) measuring diameters of their limb 2 at regular intervals along longitudinal axis L-L (a "measuring step 201"); and (ii) sending their measurements to a program operable to determine a geometrical basis for sizing apparatus 100 relative to user 1 (a "sending step 202"). Measuring step 201 may comprise physically measuring limb 2 with a measuring tape or using a 3D scanner. Sending step 202 may performed via a website and comprise executing, with a processing element (e.g., like that of user device 6), lines of code for converting the measurements into the geometrical basis.

A fit between structure 110 and user 1 may be precisely tailored based on the geometrical basis for user 1, such that sending step 202 may be following by steps for manufacturing data apparatus 100 based on the geometrical basis for user 1. For example, a curvature of each skin contact area of each skin contacting surface 118 of each node 111 (e.g., at node locations A1, A2, A3, C1, C2, and C3 of FIG. 1) and a curvature of each skin contact area of each skin contacting surface 148 of each node 141 (e.g., at node locations B1, B2, and B3 of FIG. 1) may be determined based on the geometrical basis to approximately match a particular curvature of limb 2 and skin 3 at the location where that particular node 111, 141 will be maintained when structure 110 is worn. The location of each node 111, 141, the size and location of each air gap 113, and the overall shape of structure 110 may be determined in this manner.

As shown in FIGS. 1 and 3-4, each bay 115, 145 of each node 111, 141 may contain a different data communication device 130,160 such that structure 110 may comprise a plurality of different types of nodes 111, 141 comprising a plurality of different data communication devices 130, 160. As shown in FIGS. 3 and 4, each data communication device 130, 160 may be removably contained in each bay 115, 145, each of which may comprise similar and/or different interior surfaces 124, 154 shaped to contain and position its device 130, 160. To accommodate any differences, selection step 200 may further comprise: (iii) selecting a desired set of electronic devices 130, 160 offering a desired set of functional capabilities (a "selecting step 203"). In keeping with above, selecting step 203 may be performed via a website and comprise executing, with a processing element (e.g., like that of user device 6), lines of code for converting the selections obtain in step 203 and into a separate geometrical basis for data communication devices 130, 160 that may be used to size and shape interior surfaces 124, 154 of bays 115, 145. Once steps 201-203 have been completed, procurement method 200 may comprise: (iv) converting the geometrical basis obtained in steps 202 and 203 into an estimated cost for data communication apparatus 100 based on material quantities and the selected devices 130, 160 (a "pricing step 204"). Procurement method 200 may thus be utilized by user 1 to size a data communication apparatus 100 to fit their limb 2 and perform a cost-benefit analysis regarding the desired set of functional capabilities provided therewith.

Elements of structure 110 may be manufactured from a biocompatible material (e.g., such as medical grade silicone) so that they can be safely positioned against skin 3 of limb 2 for extended periods of time. Different manufacturing methods may be used. As shown in FIGS. 1 and 3-4, nodes 111, 141 may be manufactured from a printable type of medical grade silicon using an additive manufacturing method such as 3D printing so that the shapes of bodies 114, 144 and bays 115, 145 and their material characteristics (e.g., elasticity, flexibility, etc.) may be varied to accommodate different positions of node 111, 141 on limb 2 and/or the different types of data communication devices 130, 160 contained therein. Nodes 111, 141, and cords 112 may be manufactured together, as one geometrically complex structurally interconnected shape, from one quantity and/or type of medical grade silicone material, as part of the same additive manufacturing method such as 3D printing. For example, each sidewall 119, 149 of each body 114, 144 may be 3D printed together with an end of each cord 112 extending outwardly therefrom. The geometry of the interconnected shape and/or the type of medical grade silicone may be customized to provide structure 110 with a desired amount of flexibility, elasticity, and/or rigidity. For example, any cord 112 may be 3D printed together with one of sidewalls 119, 149 to have a cord sidewall 120 that is thicker at sidewalls 119, 149 to enhance their rigidity and thinner at a central portion of cord 112 to enhance its flexibility. Accordingly, if nodes 111, nodes 141, and cords 112 are made with the same medical grade silicone using the same additive manufacturing process, then their elastic properties, and those of structure 110, may be determined at any time based on one or more of: known material properties of the medical grade silicone; measurements of the complex 3D geometry associated therewith; and/or an estimated amount of heat applied to the silicone material during the manufacturing process and over time.

Elements of electrical network 180 may be manufactured from an electrically conductive material, such as copper and/or graphene, that is compatible with the biocompatible material utilized to make structure 110. Different manufacturing methods may be used. As shown in FIG. 2, electrical network 180 may comprise a geometrically complex structurally interconnected shape sized to fit neatly within the interconnected shape defined by structure 110. Electrical network 180 may be manufactured together with nodes 111, nodes 141, and cords 112 as part of a manufacturing method 210. In keeping with above, manufacturing method 210 may comprise: (i) partially 3D molding, forming or printing nodes 111, nodes 141, and cords 112 so that a portion (e.g., a half) of lumens 120 and bays 115, 145 is laid open (a "a preparation step 211"); (ii) locating electrical network 180 in the open portion of lumens 120 and bays 115, 145 (a "locating step 212"); (iii) full forming, molding or 3D printing the remaining nodes 111, nodes 141, and cords 112 around electrical network 180, such that all of conductors 181 and substantially all of conductive rings 182 of electrical network 180 are surrounded by structure 110 and thus electrically insulated from user 1 during operation of data communication apparatus 100 (a "finishing step 213").

Preparation step 211 and finishing step 213 may comprise forming, molding or 3D printing nodes 111, nodes 141, and cords 112 together as one geometrically complex structurally interconnected shape from a quantity of biocompatible base material, such as a formable, moldable, or 3D printable material that includes medical grade silicon or is similarly biocompatibility with skin 3. Locating step 202 may comprise placing electrical network 180 into the open portion of the geometrically complex structurally interconnected shape. Locating step 212 may comprise: (iv) forming electrical network 180 by any method of manufacture (a "forming step 214"). For example, forming step 214 may comprise arranging conductors 181 and conductive rings 182 into a shape corresponding with the open portion of the geometrically complex structurally interconnected shape and attaching the ends of each conductor 181 to each conductive ring 182. Alternatively, forming step 214 also may comprise forming electrical network 180 into the open interconnected shape obtained in step 211 from a flowable and/or formable conductive material (e.g., a graphene based material). For example, forming step 214 may comprise: directing a flowable conductive material into the open portion of the geometrically complex structurally interconnected shape; or 3D printing electrical network 180 into the open portion of the geometrically complex structurally interconnected shape utilizing a 3D printable conductive material.

Data communication devices 130, 160 may be manufactured so that their operational components 135, 165 are fully contained within their respective housings 132, 162, making each 130, 160 a stand-a-alone component of data communication apparatus 100 that may be removed from structure 110 if damaged and/or no longer desired. Data communication devices 130, 160 may thus be manufactured by one or more different suppliers and then shipped to wherever manufacturing method 210 is being performed (e.g., for a new build) and/or where user 1 is located (e.g., for repair or modification). Accordingly, manufacturing method 210 may further comprise: inserting each data communication device 130, 160 into one bay 115, 145 in a direction along node axis N-N (an "inserting step 215"); containing the data communication devices 130, 160 in bays 115, 145 (a "containing step 216"); and sealing bay 115, 145 to prevent moisture from affecting data communication device 130, 160 and/or electrical network 180 (a "sealing step 217").

As shown in FIG. 3, inserting step 215 may comprise placing the contact surface of electrical contact 131, 161 of data communication device 130, 160 adjacent the contact surface of conductive ring 182 of bay 115, 145 in order to electrically connect device 130, 160 to electrical network 180. Containing step 216 may comprise elastically deforming resilient lip 125, 155 to admit data communication device 130, 160 into bay 115, 145 and expanding lip 125, 155 to maintain data communication device 130, 160 in bay 115, 145. Additional removal and/or replacement steps may be similarly performed as needed to install and swap out any data communication device 130, 160 with another device 130, 160 and/or complementary technologies, such as additional processing or power storage devices. Sealing step 217 may comprise establishing a moisture tight seal between an edge portion of skin facing surface 133, 163 and an interior surface of resilient lip 125, 155.

Manufacturing method 210 may comprise any additional steps required to initialize data communication devices 130, 160 and/or electrical network 180 once data and power is able to move therebetween. For example, method 210 also may comprise additional initialization steps such as: establishing data communication 4 between data communication apparatus 100 and application 5 of user device 6; updating the firmware of apparatus 100 and/or the software of application 5; and further customizing the performance of apparatus 100 with application 5.

As shown in FIG. 1, after completion of method 210, plurality of nodes 111, 141 may be spaced apart from one another in a 2D array or grid so that plurality of air gaps 113 are defined relative to a minimum spacing between nodes 111, 141. Because of the elasticity of cords 112, the 2D array or grid may be wrapped around limb 2 to define a 3D array or grid with approximately the same minimum spacing between nodes 111, 141. Plurality of air gaps 113 may thus be described as volumes of air located between interior surfaces of nodes 111, 141 and cords 112 when structure 110 is worn on limb 2 to maintain the minimum spacing between nodes 111, 141. As shown in FIG. 1, the material composition of plurality of cords 112 and/or these volumes of air may be sized to physically and electrically isolate each node 111, 141 from the next so that energies output with operational components 135, 165 of one node 111, 141 are less likely to affect operational components 135, 165 of another node 111, 141. Each node 111, 141 may have a diameter centered on its node axis N-N and be spaced apart from each other node 111, 141 so that a minimum spacing between each node axis N-N is at least twice the diameter. For example, each node 111, 141 may have a diameter of 3 mm with a node axis N-N spaced apart from every other node axis N-N by approximately 6 mm, making the edges of nodes 111, 141 at least 1 mm apart.

As shown in FIG. 1, exemplary locations of plurality of nodes 111, 141, plurality of cords 112, and plurality of air gaps 113 may be described with reference to a set of three columns A, B, and C intersecting a set of three rows 1, 2, and 3 to define a set of node locations A1, A2, A3, B1, B2, B3, C1, C2, and C3. One node 111, 141 may be located at each of these node locations to position a different data communication device 130, 160 on or adjacent the portion of skin 3 at that location. In keeping with above, data communication device 130, 160 may comprise similar or different operational components 135, 165 so that the capabilities of data communication apparatus 100 may be varied by utilizing different devices 130, 160. Structure 110 may thus be wearable in a similar way by a plurality of users 1, such as around the forearm or limb 2, and yet uniquely adapted to meet the needs of each user 1.

Operational aspects of data communication apparatus 100 are now described. As shown in FIGS. 1-4, data communication apparatus 100 may be operable to maintain one or more data feedback loops with user 1 such as the "haptic loops" described herein. Closed and open data feedback or haptic loops may be maintained. For example, control system 190 may utilize contextual data captured from sensor 137, such physiological measure of user 1 captured from a position on or adjacent skin 3, to maintain a closed haptic feedback loop with user 1 by communicating a first pattern and/or intensity of one or more haptic energies to nerves associated with skin 3, responsive to the contextual data, with outputs from energy generators 136, 166 at their respective locations on limb 2. As a further example, control system 190 also may utilize contextual data captured from sensor 137, 167, such as a chemical, electrical, physical, and/or physiological measure of user 1 and/or their environment, to maintain an open haptic feedback loop with user 1 by communicating a second pattern and/or intensity of one or more haptic energies to the nerves associated with skin 3 of user 1 responsive to the contextual data with outputs from one or more energy generators 136, 166 at their respective locations on limb 2. Each haptic loop may be triggered by a particular set of contextual data (from user 1 and/or their environment) and maintained by a distinguishable set of haptic energies so that data communication device 100 may be utilized to simultaneously maintain a plurality of haptic loops.

Operational aspects of data communication apparatus 100 may be described with reference to a data communication method 220 comprising: (i) causing, with controllers 138, 168, a data processing application to generate a control signal for data communication apparatus 100 (a "causing step 221"); (ii) receiving, with controllers 138, 168, the control signal from the data processing application (a "receiving step 222"); (iii) causing, with controllers 138, 168, one or more energy generators 136, 166 to output energies to skin 3 responsive to the control signal (a "causing step 223"); (iv) capturing, with a sensor in data communication with controllers 138, 168, contextual data associated with user 1 at times proximate to when the one or more energy generators 136, 166 are outputting the energies to skin 3 ("a capturing step 224"); (v) sending, with controllers 138, 168, the contextual data to the data processing application (a "sending step 225"); (vi) causing, with controllers 138, 168, the data processing application to modify the control signal responsive to the contextual data (a "modifying step 226"); (vii) receiving, with controllers 138, 168, the modified control signal from the data processing application (a "receiving step 227"); and (viii) repeating causing step 223 to cause, with controllers 138, 168, another one or more energy generators 136, 166 to output their energies to skin 3 responsive to the modified control (a "repeating step 228").

The "data processing application" of causing step 221 may comprise any elements of control system 190, such as application 5 of user device 6. As shown in FIG. 1, causing step 221 may be performed by utilizing application 5 to generate, with controllers 138, 168, instructions for causing one or more energy generators 136, 166 to output their energies during a period of time (e.g., 0.10 to 0.50 s). Receiving step 222 may be performed over wireless network 7 to initiate the period of time utilizing a transceiver of controllers 138, 168 and a wireless transceiver of user device 6. Causing step 223 may be performed with controllers 138, 168 during the period of time by utilizing the firmware of data communication device 100 to transmit data and/or power to data energy generators 136, 166 according to the instructions. Capturing step 224 may be performed during the period of time by utilizing the firmware of data communication apparatus 100 to transmit data and/or power to data to sensors 137, 167 Sending step 225 may be performed during the period of time over wireless network 7 utilizing the transceivers of controllers 138, 168 and user device 6. Modifying step 226 may be performed during the period of time by utilizing application 5 to generate a new data that is based on the contextual data and operable with controllers 138, 168 to cause a similarly and/or different set of one or more energy generators 136, 166 to output their energies during a subsequent period of time (e.g., another 0.10 to 0.50 s), possibly with different magnitudes and/or locations. Receiving step 227 may be performed towards an end of the period of time over wireless network 7 utilizing the transceivers of controllers 138, 168 and device 6. Repeating step 228, like step 223, may be performed during the subsequent period of time by utilizing the firmware of data communication apparatus 100 to transmit data and/or power to data communication devices 130, 160 over electrical network 180.

In this example, application 5 of user device 6 and the firmware of data communication apparatus 100 may work together to communicate with user 1 responsive to the contextual data from capturing step 224 by affecting the energies output to skin 3 during causing step 223. Application 5 and/or the firmware may be modified in context-specific ways to maintain one or more data feedback loops with user 1 by modifying the performance of data communication device 100 so that it reacts differently the contextual data during each successive period of time. Different types of application 5 may be implemented in this manner, any of which may be further enhanced with any type of coding languages and/or AI-powered architectures available to generate and maintain the one or more data feedback loops. Accordingly, by utilizing application 5 as an intermediary between data communication apparatus 100 and user device 6, the functional capabilities of data communication apparatus 100 provided by data communication devices 130, 160 as well as the processing capabilities of data communication apparatus 100 provided by controllers 138, 168 and external device 6 may be customized by user, rendering data communication device 100 operable to maintain any number of different data feedback loops.

When data communication method 220 is performed, the one or more data feedback loops may allow user 1 to realize certain performance advantages that are otherwise not easily obtainable, such as: faster reaction times to detectable stimulus; enhanced reactivity to data associated with a stimulus that is otherwise just outside of a detectable range; a newfound reactivity to data associated with an otherwise undetectable stimulus; and/or enhanced communications with AI-powered technologies. The processing steps handled by the firmware of operating controllers 138, 168 and application 5 of external device 6 may be modified as needed to accommodate and/or optimize the performance of causing step 221, receiving step 222, causing step 223, a capturing step 224, a sending step 225, a modifying step 226, a receiving step 227, and/or repeating step 228. For example, any of these steps, and any intermediate steps, may be performed at any location and/or in any order such that: a control signal is transmitted to and data output from data communication apparatus 100 at regular intervals (e.g., multiple times per second), allowing for continuous iteration of the control signal based on the data utilizing any processing resources of controllers 138, 168 and/or external device 6.

As described herein, data communication apparatus 100 may be operable as data monitoring device that allows user 1 to monitor one or more data streams and take actions responsive thereto. As shown in FIG. 1, one node 111, 141 containing one data communication device 130, 160 may be located at node locations A1, A2, A3, C1, C2, and C3; and one node 141 containing one data communication device 160 may be located at node locations B1, B2, and B3. Controllers 138, 168 of devices 130, 160 may be operable together with a firmware stored locally on data apparatus 100, such as within a memory accessible to controllers 138. The firmware may comprise lines of code for communicating with an external computing device 6 utilizing a transceiver that is accessible to controllers 138, 168 and operable to receive a control signal from and send data to an application of external computing device 6 according to the lines of code. The application may comprise additional lines of code for receiving data from the firmware and/or an external data source, generating the control signal based on the received data, and outputting the control signal back to the firmware, which may then cause energy generators 136, 166 and/or touchscreen 171 to perform certain functions responsive thereto.

As shown in FIG. 1, the control signal may cause touchscreen 171 at node location B1 to display a first indicia associated with a first transaction, touchscreen 171 at node location B2 to display a second indicia associated with a second transaction, and touchscreen 171 at node location B3 to display a third indicia associated with a third transaction. Each of the first, second, and third transactions may, for example, comprise a predetermined buy and/or sell action that was established by user 1 with application 5 so that placing one of their digits on one of touchscreens 171 at node locations B1, B2, and B3, without looking at a screen of user device 6, generates initiation data that causes the buy and/or sell action to be taken. The initiation data may comprise fingerprint recognition data associated with the one digit, such as an optical and/or capacitive representation of its fingerprint. For example, each controller 138, 168 may continuously monitor one touchscreen 171 for the initiation data, receive the initiation data and the finger print recognition data when user 1 places the one digit on the one touchscreen 171, and send the initiation data and the finger print recognition data to application 5, which may cause the buy and/or sell action to be taken based on the fingerprint recognition data.

In a stock trading scenario, for example, the control signal may cause: energy generators 136, 166 at node locations A1, B1, and C1 to continuously output a first energy signal with one or more different energy types responsive to a fluctuating market price of the first transaction; energy generators 136, 166 at node locations A2, B2, and C2 to continuously output a second energy signal with one or more different energy types responsive a fluctuating market price of the second transaction; and energy generators 136, 166 at node locations A3, B3, and C3 to continuously output a third energy signal with one or more different energy types responsive to a fluctuating market price of the third transaction. The predetermined buy and/or sell action established by user 1 may comprise a lower threshold associated with column 1 and an upper threshold associated with column 3, such that: (i) movements of the first, second, and third energy signals in a first direction around rows A, B, and C (e.g., a clockwise direction relative to limb 2) may communicate price decreases; and (ii) movements of the first, second, and third energy signals in a second direction around rows A, B, and C (e.g., a counterclockwise direction relative to limb 2) may communicate price increases. For each of the first, second, and third transactions, price increases may thus be communicated to user 1 when the respective first, second, and third energy signals are located at and/or moving toward node locations A1, B1, and/or C1; and price decreases may be similarly communicated to user 1 when the respective energy signals are located at and/or moving toward node locations A3, B3, and/or C3.

A magnitude and/or energy type of the first, second, and third signals at any of their respective node locations A1-A3, B1-B3, and C1-C3 may be modified responsive the control signal in order to communicate a magnitude of a particular price increase or decrease. For example, when moving in the first direction toward node location A1, the first energy signal may be comprise: (i) a first moving portion output with energy generator 136, 166 at node location A2 for a first period of time (e.g., 2 s) with one combination of energy types at one magnitude, communicating to user 1 that a first minimum degree of price increase has occurred; and (ii) an second moving portion output with energy generator 136, 166 at node location A3 for a second period of time (e.g., 2 s) with another combination of energy types at another magnitude, communication to user 1 that a second minimum degree of price increase has occurred. In this example, the magnitude and/or energies of the additional portion output at node location A3 may be increased and/or modified at intervals of time (e.g., 2 s) as the price increase approaches the upper threshold; and further increased and/or modified at the time internals when the upper threshold is exceeded, further communicating to user 1, with pain if necessary, that the time for action is now.

In the stock trading scenario, if a trader happens to walk away from their data monitoring screens while wearing data communication apparatus 100, then they can utilize the energy generators 136, 166 to monitor the same market data and touchscreens 171 to take the same buy and/or sell actions that they otherwise would if they had not walked away. Any corresponding type of data and actions may be similarly monitored and taken with data communication apparatus 100, such that aspects described here are not limited by this example and may be similarly applicable to any analogous decisions based on similar streams of data.

The data gathering capabilities of data communication apparatus 100 may provide numerous opportunities to verify that each buy and/or sell action was intentionally taken by user 1 when the initiation data was received. As shown in FIG. 1, example, the contact sensing surface of one touchscreen 171 at node location A1 may be operable as a first identity verification sensor to capture the fingerprint identification data when user 1 places their one digit on the first indicia displayed by touchscreen 171 at node location A1, allowing its controller 138, 168 to send the fingerprint identification data to application 5 for processing with a neural network trained to identify user 1 based on the fingerprint identification data.

Sensor 172 may be operable as a second identity verification sensor to capture facial recognition data when user 1 places their one digit on touchscreen 171 at node location A1. To continue the previous example, sensor 172 at node location A1 may be blocked when the one digit contacts touchscreen 171 at location A1, causing another one of sensors 172 (e.g., node locations A2 and/or A3) to capture the facial recognition data, allowing its controller 138, 168 to send the facial recognition data to the application 5. Sensors 137, 167 may be operable as a third identity verification sensor. Continuing the previous example, any of sensors 137, 167 at node locations A1-C3 may be operable to capture physiological data from skin 3 when user 1 places their one digit on touchscreen 171 at location A1, allowing one or more of controllers 138, 168 to send the physiological data to application 5 for processing with a neural network trained to identify user 1 based on the physiological pattern data. The physiological data may comprise a pattern of vital sign data, images of vein structures, identifying skin features, and/or any other type of data that is capturable by sensor 137, 167 processable by an appropriately trained neural network.

The data gathering capabilities of data communication apparatus 100 may provide numerous opportunities to continuously capture additional contextual data associated with user 1, any of which may be sent to application 5 for further processing. The optical and/or camera elements of sensor 172 may be operable as an environmental scanner operable to capture contextual data at times that may or may not be related to when user 1 places their one digit on the first indicia displayed by touchscreen 171 at location A1, allowing controllers 138, 168 to send the contextual data to application 5 for processing with a neural network trained to identify user 1's environment based on the contextual data, such as by recognizing various persons and/or objects.

To continue the ongoing example, sensors 137, 167 at node locations B1, B2, and B3 may intermittently capture contextual data comprising images, sounds, geolocating data (e.g., GPS signals), Wi-Fi communication data (e.g., IP addresses), security access data, and/or any other type of contextual data that may be similarly processed, providing other ways to identify user 1 and confirm their intentions. As a further example, sensor 172 also may comprise one or more microphones positioned to capture contextual data including a recording of user 1's voice at times before and after when user 1 places their one digit on the first indicia displayed by touchscreen 171 at location A1, allowing controllers 138, 168 to send the contextual data to application 5 for processing with a neural network trained to determine what user 1 is saying in relation the action, providing additional opportunities for verification.

Aspects are now described with reference to variations of data communication apparatus 100 that are functionally similar to those described in above, but with select modifications to intended to modify the structures of and/or functions performable with data communication apparatus 100. The variations include: an exemplary data communication apparatus 400 shown in FIG. 5; an exemplary data communication apparatus 500 shown in FIG. 6; an exemplary data communication apparatus 600 shown in FIG. 7; an exemplary data communication apparatus 700 shown in FIG. 8; an exemplary data communication apparatus 800 shown in FIG. 9; and an exemplary data communication apparatus 900 shown in FIG. 10.

Each variation of data communication device 100 described herein, such as apparatus 400, 500, 600, 700, 800, and 900, may include elements similar to those of apparatus 100, but within the respective 400, 500, 600, 700, 800, or 900 series of numbers, whether or not those elements are shown. Any aspects now described with reference data communication apparatus 400, 500, 600, 700, 800, and 900 may be included within any variation of apparatus 100 described herein, each possible combination or iteration being part of this disclosure. For example, any data communication apparatus 100, 400, 500, 600, 700, 800, and 900 now described may be similarly obtained with procurement method 200, manufactured with manufacturing method 210, and/or operable with data communication method 220.

Figure 5:
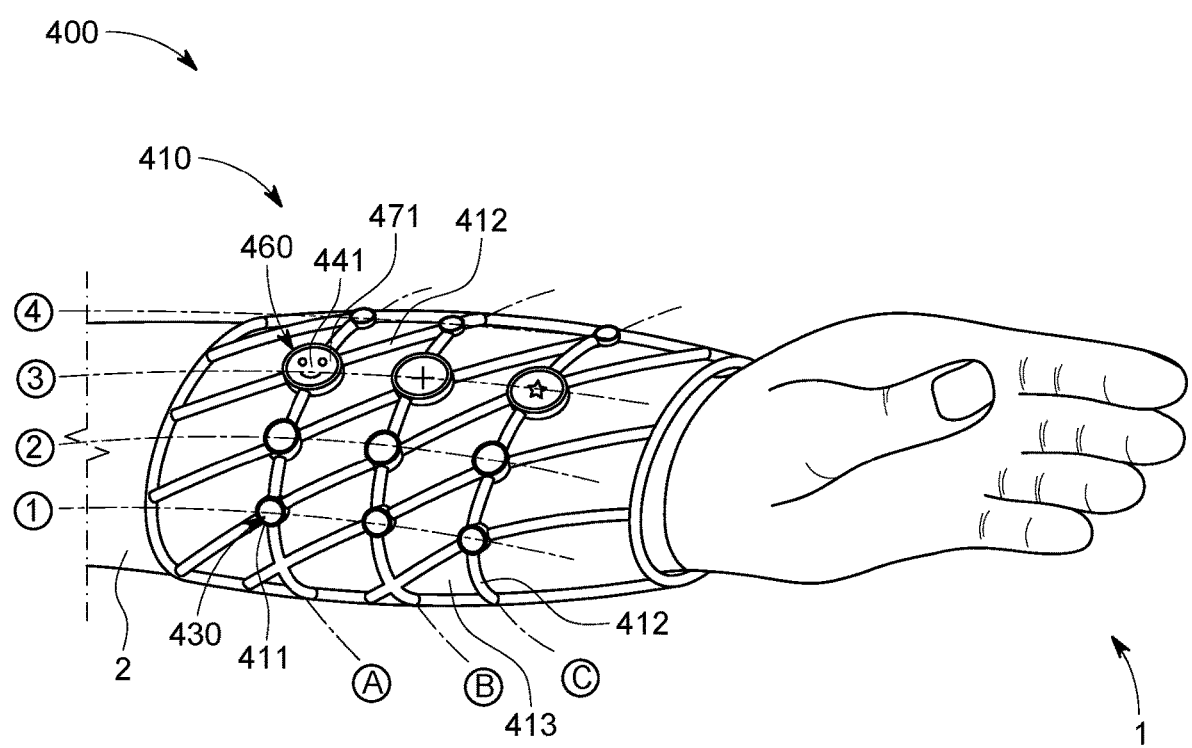
FIG. 5 depicts another exemplary wearable data communication apparatus.

As shown in FIG. 5, data communication apparatus 400 may comprise a structure 410 with a plurality of nodes 411, 441, a plurality of cords 412, a plurality of air gaps 413, data communication devices 430, 460, and an electrical grid 480, each of which may be similar to counterpart elements of data communication apparatus 100 except for the differences now described.

Structure 410 may be shaped to define and/or part of a wearable cuff, sleeve, or similar wearable object. As shown in FIG. 5, plurality of cords 412 may comprise circular rings and lateral segments that are interconnected with one another to define a generally cylindrical shape that extends along a longitudinal axis L-L of limb 2 when worn. Each circular ring may be coaxial longitudinal with axis L-L. Structure 410 may have length of approximately 3" to 8" extending between a proximal circular ring adjacent the elbow and a distal circular ring adjacent the wrist. As shown in FIG. 5, each circular ring may comprise a row of nodes 411, 441 (e.g., shown in FIG. 5 as rows A, B, and C) spaced apart from one another. Each row of nodes 411, 441 may extend partially or fully around limb 2 on its respective circular ring. Each lateral segment may be engaged with nodes 411, 441 in a direction that intersects the circular rings, helping to brace each node 411, 441 and maintain a shape of structure 410.

A cross-section of the circular rings may be different from (e.g., larger and/or thicker) a cross-section of the lateral segments so their elastic characteristics are different. For example, each circular ring of nodes 411, 441 may have an enhanced elasticity that allows it to expand when receiving limb 2 and then contract around limb 2 after receiving limb 2, much like a rubber band, allowing structure 410 to conform around the generally circular shape of limb 2 and continually cause radially directed forces that press the skin contacting surfaces 423, 453 of nodes 411, 441 against skin 3 with a normal force greater than that applicable to skin 3 by the lateral segments. The proximal and distal rings may be similarly modified.

As shown in FIG. 5, structure 410 may provide a robust platform for data communication devices 430, 440 that is suitable for recreational and professional use. The intersecting circular rings and lateral segments of plurality of cords 412 may provide additional opportunities for customizing their elastic characteristics and thus those of structure 410. Structure 410 may thus be fitted to any size or shape of limb 2 and further customize to obtain a tighter fit, as may be required when data communication apparatus 400 is worn while playing sports. As shown in FIG. 5, structure 410 may be a stand-alone accessory, contained within a fabric veneer (e.g., such as an arm band), and/or embedded in another piece of clothing or wearable items (e.g., a sleeve). The rows of nodes 411, 441 may be spaced apart by distance that allows them to communicate distinguishable energy signals to skin 3.

The orientation and spacing of nodes 411, 441 in each row may allow for directional communications around limb 2. As shown in FIG. 5, nodes 411, 411 in rows A, B, and C may be similarly organized into columns 1, 2, 3, 4, and 5, thereby defining node locations A1-A5, B1B-5, and C1-C5. In keeping with the stock trading scenario described above, node locations A3, B3, and C3 may comprise nodes 441 with touchscreens 471; and touchscreen 471 at node location A3 may display a first indicia associated with a first transaction, touchscreen 471 at node location B3 may display a second indicia associated with a second transaction, and touchscreen 471 at node location C3 may display a third indicia associated with a third transaction. As shown in FIG. 5, the additional node locations in columns 1-2 and 4-5 may similarly communication price increases and/or decreases, but with longer movements of the first, second, and third energy signals in directions around rows A, B, and C.

Figure 6:
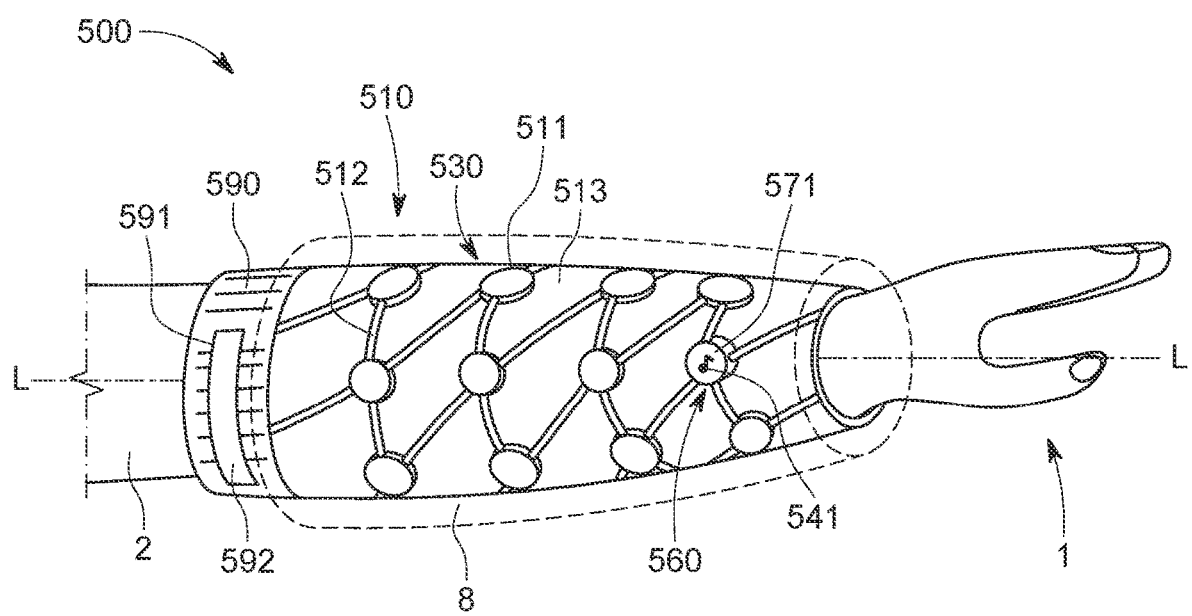
FIG. 6 depicts another exemplary wearable data communication apparatus.

As shown in FIG. 6, data communication apparatus 500 may comprise a structure 510 with a plurality of nodes 511, 541, a plurality of cords 512, a plurality of air gaps 513, data communication devices 530, 560, and an electrical grid 580, each of which may be similar to counterpart elements of data communication apparatus 100 except for the differences now described.

Data communication apparatus 500 may be operable to output healing energies to limb 2. As shown in FIG. 6, structure 510 may be worn on a broken limb 2 underneath and/or as a cast 8. Plurality of cords 512 and nodes 511, 541 may intersect one another to define a generally cylindrical shape that extends along a longitudinal axis L-L of limb 2 when structure 510 is worn. Each element of structure 510, including cords 512 and nodes 511, 541, may comprise a biocompatible material (e.g., like medical grade silicon) that can be maintained against skin 3 for a treatment regime spanning a longer period of time, such as 6 to 8 weeks. The elastic characteristics of structure 510 may provide it with a greater degree of flexibility, making it easier to don structure 510 without contorting broken limb 2. Cast 8 may formed around structure 510 using conventional methods, such as with layers of cotton, plaster, fiberglass, and/or additional splinting elements. Alternatively, the elastic characteristics of structure 510 may provide it with a greater degree of rigidity so that the bracing and support functions of cast 8 may be provided entirely by structure 410. For example, the generally cylindrical shape defined by plurality of cords 512 and nodes 511, 541 may be 3D printed from a more rigid material (e.g., ABS or PLA) to provide a thin, breathable, customizable, waterproof, easily removable structure 510 that is operable as cast 8 to similarly prevents infection and muscle atrophy.

As shown in FIG. 6, structure 510 may comprise a plurality of nodes 511 and also may comprise a node 541. Each node 511 may comprise an outward facing surface 517 engageable with an outer covering such as cast 8 and a communication bay 515 containing one data communication device 530. Similar to as shown in FIG. 3, each data communication device 530 may comprise a haptic energy generator 536 operable to output different types of haptic energy toward skin 3, such as electricity, thermal, and/or vibrational energies. At least one node 541 may comprise an outward surface 547 that protrudes beyond an outer surface of cast 8 and a communication bay 545 containing one data communication device 560. Similar to as shown in FIG. 4, each data communication device 560 may comprise a haptic energy generator 566 operable to output different types of haptic energy toward skin 3, such as electricity, thermal, and/or vibrational energies; and a touchscreen 571 operable to cause haptic energy generators 536, 566 to output their respective energies toward skin 3.

The energies output from haptic energy generators 536, 566 may promote healing of broken limb 2 and surrounding tissues by stimulating bone growth and tissue repair. For example, data communication apparatus 500 may be operable with application 5 to prompt user 1 to begin a treatment period by displaying indicia on touchscreen 571. User 1 may place one of their digits on touchscreen 571 to begin the treatment period, causing energy generators 536, 566 to output their haptic energies at different locations on limb 2 with different haptic energy types and/or magnitudes according to a predetermined pattern or sequence of haptic energy types described herein as a "haptic track." For example, application 5 may receive a selection of user 1's favorite song, generate the haptic track based on the selected song, and cause haptic energy generators 536, 566 to output their energies in time therewith. As further example, application 5 also may cause an audiovisual device (e.g., headphones) to play the song in time with the haptic energies as a means for distracting user 1's attention from any pain caused by the energies and increasing their likelihood of compliance.

As shown in FIG. 6, data communication apparatus 500 also may comprise a proximal sleeve 590, a battery housing 591, and a battery 592. Proximal sleeve 590 may comprise an elastic element operable to help maintain a position of structure 510 on limb 2 and prevent moisture from entering cast 8, similar to a sweat band. Battery housing 591 may be electrically connected to electrical network 580 and comprise structures for removably engaging battery 592 to sleeve 590. Battery 592 may be large enough to power data communication devices 530, 560 for an extended period of time and/or allow for higher intensity outputs. Because it is removable, battery 592 may be easily swapped out by user 1 to facilitate ongoing (e.g., daily) usage of data communication apparatus 500 during the treatment regime.

Figure 7:
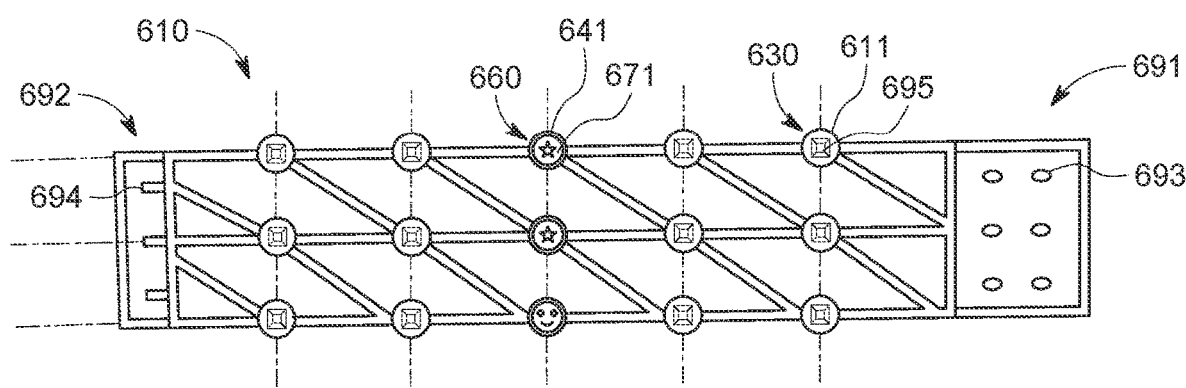
FIG. 7 depicts another exemplary wearable data communication apparatus.

As shown in FIG. 7, data communication apparatus 600 may comprise a structure 610 with a plurality of nodes 611, 641, a plurality of cords 612, a plurality of air gaps 613, data communication devices 630, 660, and an electrical grid 680, each of which may be similar to counterpart elements of data communication apparatus 100 except for the differences now described.

Structure 610 may be shaped to define and/or part of a wearable cuff, sleeve, or similar wearable object. As shown in FIG. 7, plurality of cords 612 and a plurality of nodes 611, 641 may be interconnected to define a generally rectangular shape that may be wrapped around limb 2 about longitudinal axis L-L. In contrast to above, structure 610 may further comprise a first engagement structure 691 at a first end of the generally rectangular shape and a second engagement structure 692 at a second end of the generally rectangular shape. First engagement structure 691 may comprise openings 693 and second engagement structure 692 may comprise hooks 694 that are receivable in openings 693. User 1 may don structure 610 by wrapping it around limb 2 and receiving hooks 694 in openings 693. The normal forces applied by skin contacting surfaces 623, 653 of nodes 611, 641 may thus be determined based on the elastic characteristics of structure 610 and the interaction between openings 693 and hooks 694. First and second engagement structures 691, 692 may comprise any type of interconnecting structures, including openings 693 and hooks 694, any alternative hook and look structures (e.g., such as Velcro®), and/or any other fastening means.

First and second engagement structures 691, 692 also may be engageable with another wearable item. For example, structures 691, 692 may be removable engageable with a belt that includes additional fastening means and/or serve as the fastening means (e.g., as a belt buckle). First and second engagement structures 691, 692 also may be operable with additional structures 691, 692 of an additional data communication device 600 so that a plurality of devices 600 may be connected along their respective lengths in a daisy chain that is long enough wrap around a larger portion of user 1, such as their chest, head, or torso.

As shown in FIG. 7, each node 611 of structure 610 may comprise an outward facing surface 617 with an adornment 695 and a communication bay 615 containing one data communication device 630. Data communication apparatus 600 may thus comprise a plurality of adornments 695. Similar to as shown in FIG. 3, each data communication device 630 may comprise a haptic energy generator 636. As also shown in FIG. 7, each node 641 may comprise an outward facing surface 647 and a communication bay 645 containing one data communication device 660. Similar to as shown in FIG. 4, each data communication device 660 may comprise a haptic energy generator 666 and a touchscreen 671 positioned adjacent surface 647.

Adornments 695 may provider user 1 with additional opportunities to customize data communication apparatus 600, making it a functional piece of jewelry. Each adornment 695 may comprise objects such as jewels, LED lights, or other types of "bling" mounted to outward facing surface 617. As shown in FIG. 7, each adornment 695 may be fixedly or removably engaged with surface 617, allowing them to be replaced. Any node 611 may comprise an adornment 695, including nodes 641, which may incorporate adornments 695 into outward facing surface 647. Some adornments 695 may comprise an electronic device, such a light source, touchscreen, and/or sensors, providing additional ways to customize the look and functionality of data communication apparatus 600. For example, each adornment 695 may be sold separately of and/or in a kit together with other adornments 695, data communication apparatus 600, and/or any other design elements engageable therewith, including any decorative elements (e.g., bedazzling or gems), graphic elements (e.g., paint, prints, or stickers), and/or fabric attachment elements (e.g., Velcro portions).

As shown in FIG. 7, each outward facing surface 617, 647 of each node 611, 641 may thus provide a different place for incorporating a different adornment 695. Any visual media and/or technology may be incorporated into adornments 695, including instruction elements relating to actions performable with touchscreens 671, QR codes for identifying user 1 to a machine vision-enabled camera, instructions for operating apparatus 600, and/or purely decorative elements. The color of structure 610 and/or each component thereof, including nodes 611, 641, may be similarly customized. Other elements also may be attached to or worn over structure 610 for like purposes. For example, some adornments 695 may comprise functional attachments operable with another garment, such as Velcro attachments operable with an interior surface of fabric sleeve that may be slipped over and/or attached to structure 610.

Figure 8:
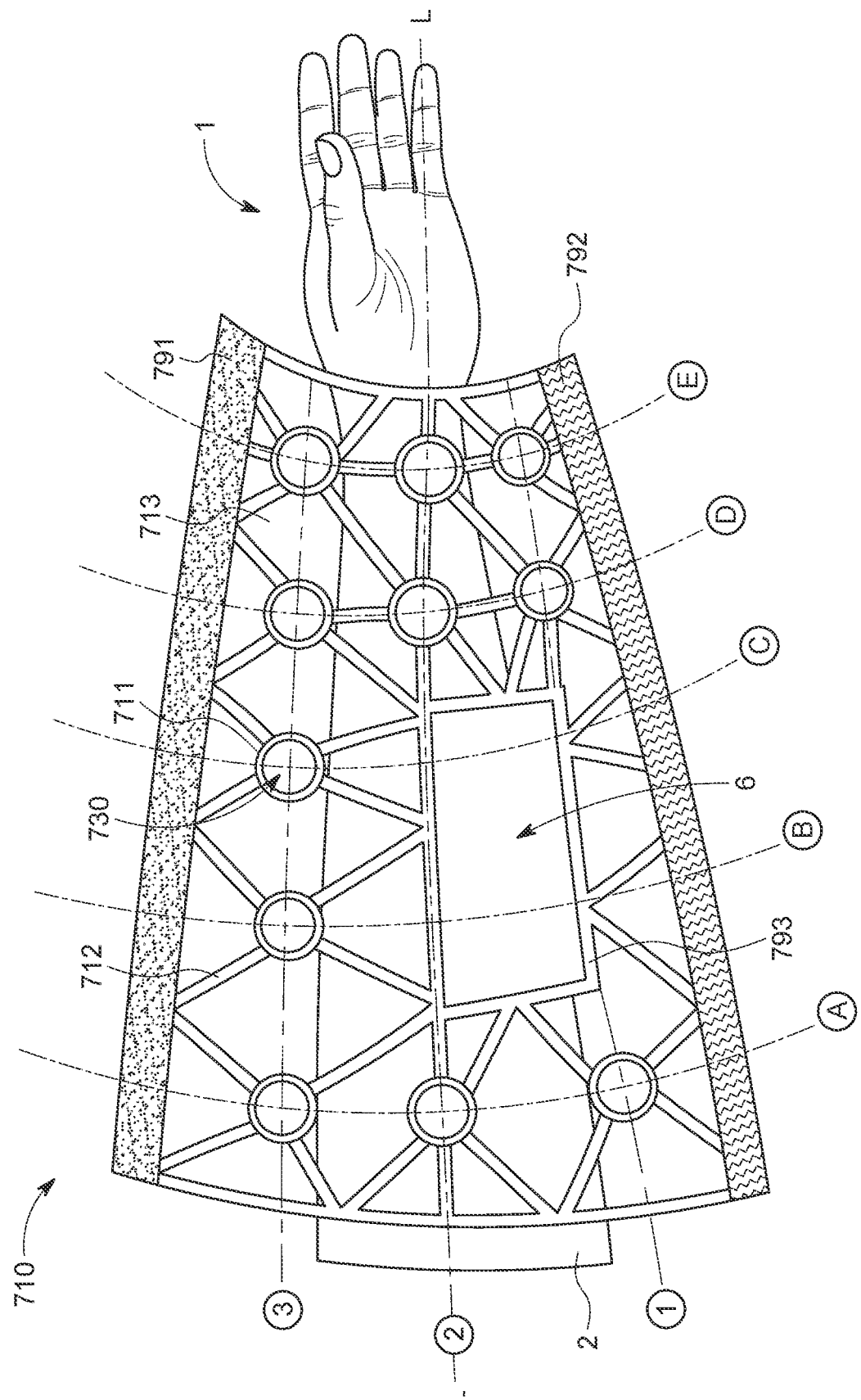
FIG. 8 depicts another exemplary wearable data communication apparatus.

As shown in FIG. 8, data communication apparatus 700 may comprise a structure 710 with a plurality of nodes 711, a plurality of cords 712, a plurality of air gaps 713, data communication devices 730, and an electrical grid 780, each of which may be similar to counterpart elements of data communication apparatus 100 except for the differences now described.

Structure 710 may be shaped to define and/or be part of a wearable cuff, sleeve, or similar wearable object. As shown in FIG. 8, plurality of cords 712 and plurality of nodes 711 may be interconnected to define an elongated shape with an irregular array or grid pattern, such as one based on a physical geometry of limb 2. In contrast to above, structure 710 may further comprise a first engagement structure 791 extending along a first side of the elongated shape and a second engagement structure 792 extending along a second side of the elongated shape. First and second engagement structures 791, 792 may comprise any type of interconnecting structures, such as a first Velcro portion (e.g., with loops) and a second Velcro portion (e.g., with hooks). User 1 may don structure 610 by wrapping it around limb 2 and engaging structures 791 along their respective lengths. Similar to above, the normal forces applied to skin 3 by skin contacting surfaces 723 of nodes 711 may thus be determined based on the elastic characteristics of structure 710 and the interaction between structures 791, 792.

Data communication apparatus 700 also may comprise a device holder 793. As shown in FIG. 8, device holder 793 may be electrically connected to electrical grid 780 and operable to contain user device 6, allowing data and power to be transferred between device 6 and data communication devices 730. When structure 710 is worn on limb 2, first and second engagement structures 791, 792 may be located on an outer surface and device holder 793 may be located on an inner surface, making it easily accessible to digits of user 1's other hand. When mounted in device holder 793, user device 6 may be operable to enhance a functionality of data communication apparatus 700 by providing increased processing power, faster communication of data to and from data communication devices 730, and an additional power source. User device 6 may utilized to supplant the input capabilities of data communication devices 760 such that data communication apparatus 700 may consist only of nodes 711 and data communication devices 730, thereby reduce its cost by relying on the capabilities of user device 6 to control devices 730. Attaching user device 6 directly to structure 710 also provides user 1 with a secure means for operating and storing device 6.

As shown in FIG. 8, user device 6 may comprise a particular type of smartphone (e.g., an Apple iPhone) and device holder 793 may be structurally and electrically engageable with that particular type of smartphone. Device holder 793 may be manufactured together with the remainder of structure 710 and thus interconnected with plurality of cords 712. The elastic characteristics of structure 710 may be optimized to securely mount user device 6 in device holder 793 while allowing for enough flexibility so the user may move his or her forearm. Data communication apparatus 700 may comprise any number of device holders 793. For example, data communication apparatus 700 also may comprise an additional device holder 793 that is similarly operable with an additional user device (e.g., an Apple iWatch) to further expand the capabilities of apparatus 700.

Figure 9:
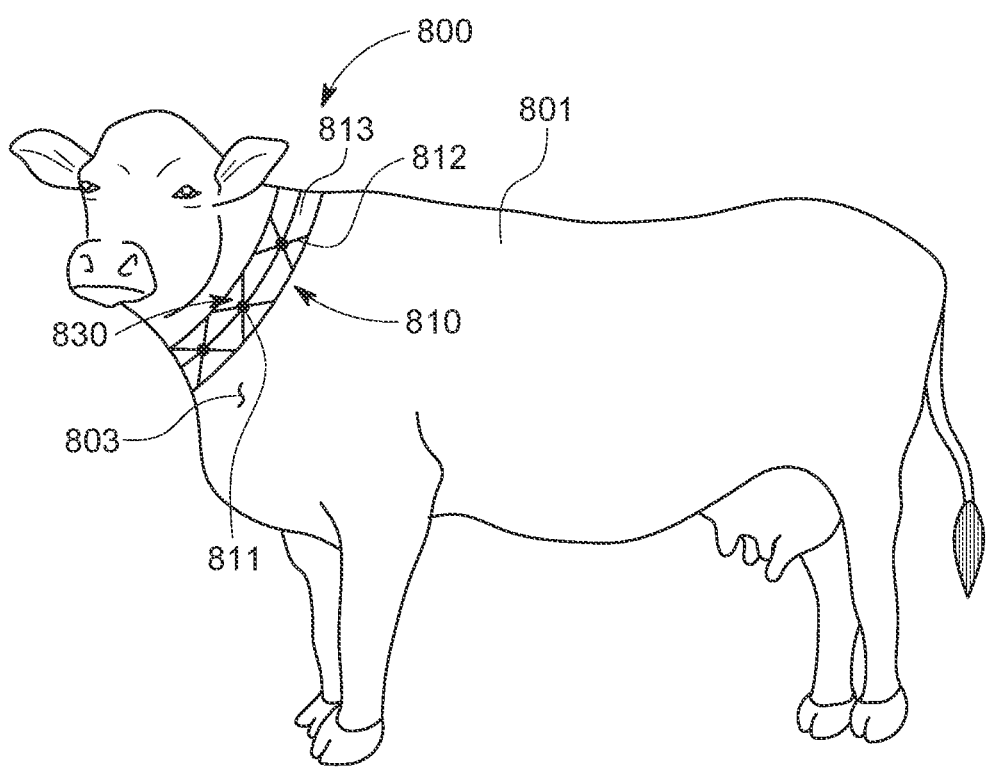
FIG. 9 depicts another exemplary wearable data communication apparatus.

As shown in FIG. 9, data communication apparatus 800 may comprise a structure 810, a plurality of nodes 811, a plurality of cords 812, a plurality of air gaps 813, data communication devices 830, and an electrical network 880, each of which may be similar to counterpart elements of data communication apparatus 100 except for the differences now described.

Structure 810 may comprise a closed or open shape sized to fit around a limb or torso of an animal 801 for the purpose of communicating haptic energy signals to animal 801 for training purposes. For example, plurality of nodes 841 may be located on each side of animal 801 and activated to guide the animal in a particular direction (e.g., left or right) responsive to one or more haptic energies output to skin 803 of animal 801 on one side or the other, provide a simple but effective means of prodding animal 801 from a remote location outside of pen. Outputs utilizing electricity and/or impact forces may be particular useful in this example. The size and power of data communication apparatus 800 may vary. For use with large animals, such as cows, sheep, and pigs, each node 841 of data communication apparatus 800 may comprise a haptic energy generator 836 that is larger and more powerful than shoe of data communication apparatus 100. Data communication apparatus 800 may be similarly operable to maintain haptic loops with animal 801, including those related to feeding times and responsive to physiological data obtained with sensor 837.

Aspects of data communication apparatus 800 may be simplified for use with animal 801. For example, apparatus 800 may consist of nodes 811 and data communication devices 830 because animal 801 cannot operable touch-screens 871. As a further example, because animals are often kept in remote areas, data communication apparatus 800 also may be operable without application 5 by utilizing an expanded firmware that automatically responds to certain inputs and/or is receptive to more generic control signals broadcast thereto over wireless network 7.

Figure 10:
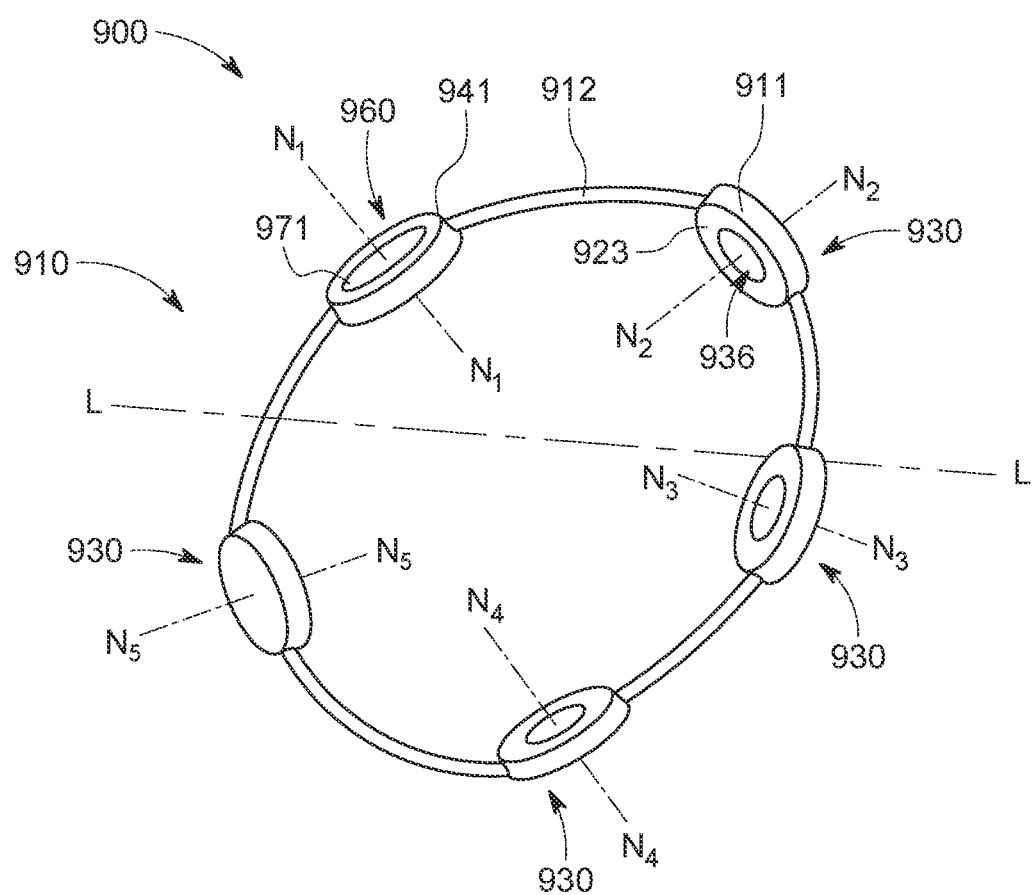
FIG. 10 depicts another exemplary wearable data communication apparatus.

As shown in FIG. 10, data communication apparatus 900 may comprise a structure 910 with a plurality of nodes 911, 941, a plurality of cords 912, a plurality of air gaps 913, data communication devices 930, 960, and an electrical grid 980, each of which may be similar to counterpart elements of data communication apparatus 100 except for the differences now described.

Aspects of data communication apparatus 900 may be further simplified. As shown in FIG. 10, structure 910 may be operable as a bracelet, headband, torso band, thigh band, and/or watch with enhanced communicative capabilities. Plurality of cords 912 may be interconnected with a plurality of nodes 911 and at least one node 941 to define a circular ring. Nodes 911, 941 may be spaced apart from one another around the circular ring. The elastic characteristics of plurality of cords 912 may be adapted to press skin contacting surfaces 923, 953 of nodes 911, 941 into skin 3 as before, helping to maintain a position of structure 910 on limb 2 in a similar manner. The elasticity of cords 912 and/or surface area of skin contacting areas 923, 953 may be increased as needed to maintain the position of structure 910. A size of structure 910 may be determined based on its intended location. For example, it is contemplated that larger sizes may be worn on the head, chest, or torso of user 1 and smaller sizes may be worn on the arm or leg. The number of nodes 911, 941 may be increased or decreased as needed to accommodate the different sizes. Because of its simplicity structure 910 also may be assembled with and/or built into another wearable item, like a headband or a hat.

Each node 911 may comprise a communication bay 915 containing one data communication device 930 and node 941 may comprise a communication bay 945 containing one data communication device 960. As shown in FIG. 10, when structure 910 is worn, node 941 may be accessible to the eyes and plurality of nodes 911 may be spaced apart therefrom, much like the circular rings of structure 910 described above, allowing for directional communication similar to those described above.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A data communication apparatus wearable on or adjacent skin of a wearer, the apparatus comprising:
 a plurality of data communication devices comprising a
  sensor operable to output contextual data associated with the wearer, a plurality of haptic energy generators operable to output a haptic energy toward the skin of the wearer, and a control system operable to maintain a data feedback loop with the wearer by causing the plurality of haptic energy generators to output the haptic energy responsive to one of the contextual data and an external data source in data communication with the control system;

an electrical network operable to transmit data and power between the plurality of data communication devices; and a wearable structure comprising a biocompatible material shaped to define a plurality of nodes, a plurality of cords extending between the plurality of nodes, and a skin contacting surface that is directly engageable with the skin;

the plurality of nodes being operable to house the plurality of data communication devices;

the plurality of cords being operable to house the electrical network, maintain a plurality of air gaps between the plurality of data communication devices, and maintain a position of the wearable structure on the wearer by pressing the skin contacting surface toward the skin when the wearable structure is worn.

2. The apparatus of claim 1, wherein the sensor comprises a plurality of sensors operable to output the contextual data.

3. The apparatus of claim 2, wherein each device of the plurality of data communication devices comprises:
one sensor of the plurality of sensors; and
one generator of the plurality of haptic generators.

4. The apparatus of claim 1, wherein the sensor comprises a physiological sensor operable to output a physiological portion of the contextual data.

5. The apparatus of claim 4, wherein the physiological sensor is oriented toward the skin of the wearer.

6. The apparatus of claim 5, wherein a portion of the physiological sensor is located on or adjacent the skin.

7. The apparatus of claim 5, wherein the physiological sensor is operable to detect one or more of a blood pressure, a body temperature, a heart rate, a perspiration rate, and a toxicity level of the wearer.

8. The apparatus of claim 4, wherein the sensor comprises an environmental sensor operable to output additional contextual data associated with the wearer or their environment.

9. The apparatus of claim 8, wherein the environmental sensor is operable to detect a chemical, electrical, or physical measure of the wearer or their environment.

10. The apparatus of claim 8, wherein the physiological sensor is oriented toward the skin of the wearer.

11. The apparatus of claim 10, wherein the environmental sensor comprises one or more of an optical sensor, a photo-sensing transistor, and a camera.

12. The apparatus of claim 10, wherein the plurality of data communication devices comprise a touchscreen and the environmental sensor is embedded within an electronic visual display of the touchscreen.

13. The apparatus of claim 10, wherein the environmental sensor comprises one or both of a geolocating technology and a motion sensing technology.

14. The apparatus of claim 1, wherein the plurality of haptic energy generators comprise a single energy haptic communication technology.

15. The apparatus of claim 1, wherein the plurality of haptic energy generators comprise a multi-energy haptic communication technology.

16. The apparatus of claim 1, wherein the plurality of haptic energy generators comprise electromagnetic components operable to output the haptic energy.

17. The apparatus of claim 1, wherein the control system comprises a controller of one of the data communication devices.

18. The apparatus of claim 1, wherein each data communication device comprises a controller and the control system comprises one or more of the controllers of the data communication devices.

19. The apparatus of claim 1, wherein each data communication device comprises a controller, the controllers of the data communication devices are located at different locations and in data communication with one another via the electrical network, and the control system comprises a distributed computing system with individual processing resources comprising the controllers of the data communication devices.

20. The apparatus of claim 19, wherein the individual processing resources of the distributed computing system comprise the external data source.

21. The apparatus of claim 1, wherein the plurality of data communication devices are removably housed in the plurality of nodes.

22. The apparatus of claim 21, wherein the plurality of data communication devices are removably housed in the plurality of nodes to facilitate repairing and upgrading the apparatus.

23. The apparatus of claim 22, wherein each device of the plurality of data communication devices comprises a conductor that electrically engages the electrical network when that data communication device is removably housed in one node of the plurality of node.

24. The apparatus of claim 23, wherein the conductors of the plurality of data communication devices are interchangeably engageable with the electric network when removably housed in any node of the plurality of nodes.

25. The apparatus of claim 1, wherein the electrical network comprises a plurality of conductive materials spanning between the plurality of data communication devices through the plurality of cords.

26. The apparatus of claim 25, wherein the plurality of conductive materials comprise metallic wires or electrically conductive filaments.

27. The apparatus of claim 1, wherein the electrical network comprises graphene.

28. The apparatus of claim 27, wherein the electrical network is 3D printed from the graphene.

29. The apparatus of claim 1, wherein the biocompatible material comprises a silicone.

30. The apparatus of claim 1, wherein:
the wearable structure defines a sleeve; and
the plurality of cords are expandable to receive a portion of the wearer in the sleeve and contractible to maintain a rotational and translational position of the sleeve on the portion of the wearer.

31. The apparatus of claim 30, wherein the plurality of cords resiliently expand and contract to obtain a close fit between the sleeve and the skin.

32. The apparatus of claim 31, wherein the plurality of nodes and the plurality of cords are 3D printed from the biocompatible material in one or more stages so that the electrical network is contained in the plurality of nodes.

33. The apparatus of claim 1, wherein the plurality of cords are contractible to press the skin contacting surface into the skin with a normal force that establishes a friction fit between the skin contact surface and the skin.

34. The apparatus of claim 1, wherein the skin contacting surface is curved to increase a contact area with the skin.

35. The apparatus of claim 1, wherein the skin contacting surface is operable to maintain a minimum coefficient of friction with the skin of the wearer.

36. The apparatus of claim 35, wherein the skin contact surface comprises one of a localized geometric feature or a biocompatible adhesive operable to maintain the minimum coefficient of friction.

37. The apparatus of claim 1, wherein the wearable structure comprises a cylindrical shape extending along a longitudinal axis.

38. The apparatus of claim 37, wherein the wearable structure is wrapped around a portion of the wearer about the longitudinal axis to define the cylindrical shape.

39. The apparatus in claim 38, wherein the wearable structure comprises a first end with a first engagement structure at a first end, a second end with a second engagement structure at a second end, and the first engagement structure is engageable with the second engagement structure to wrap the structure around the portion of the wearer.

40. The apparatus of claim 1, wherein each device of the plurality of data communication devices comprises:
a housing removably engageable with one node of the plurality nodes; and
a conductor removably engageable with the electrical network when the housing is removably engaged with the wearable structure.

41. The apparatus of claim 1, wherein one or more devices of the plurality of data communication devices comprise:
at least one sensor; and
one haptic generator of the plurality of haptic generators.

42. The apparatus of claim 41, wherein the at least one sensor comprises a physiological sensor operable to output a first portion of the contextual data.

43. The apparatus of claim 42, wherein the at least one sensor comprises an environmental sensor operable to output a second portion of the contextual data.

44. The apparatus of claim 42, wherein the physiological sensor is oriented toward the skin of the wearer.

45. The apparatus of claim 43, wherein the environmental sensor is oriented away from the skin of the wearer.

46. The apparatus of claim 1, wherein one or more devices of the plurality of data communication devices comprise a touchscreen operable to receive inputs from the wearer.

47. The apparatus of claim 46, wherein the one or more devices of the plurality of data communication devices comprise:
at least one sensor; and
one haptic generator of the plurality of haptic generators.

48. The apparatus of claim 46, wherein the touchscreen comprises an electronic visual display and a contact sensing surface.

49. The apparatus of claim 48, wherein the electronic visual display is operable to display an icon and the contact sensing surface is operable to detect a gesture applied to the touchscreen by a finger of the wearer.

50. The apparatus of claim 49, wherein the contact sensing surface comprises a fingerprint sensor operable to detect a fingerprint of the finger when applying the gesture.

51. The apparatus of claim 50, wherein the plurality of data communication devices comprise a location sensor operable to determine a location of the apparatus when the fingerprint is detected with the fingerprint sensor.

52. The apparatus of claim 51, wherein the plurality of data communication devices comprise a camera operable to capture a picture of the wearer when the fingerprint is detected with the fingerprint sensor.

53. The apparatus of claim 52, wherein the control system is operable to confirm an identify of the wearer based on one of the fingerprint, the location, and the picture.

\* \* \* \* \*